United States Patent
Gallardo Sánchez et al.

(10) Patent No.: US 8,945,522 B2
(45) Date of Patent: Feb. 3, 2015

(54) SILYL POLYMERIC BENZOIC ACID ESTER COMPOUNDS, USES, AND COMPOSITIONS THEREOF

(75) Inventors: Adaya Gallardo Sánchez, Sant Cugat del Vallés-Barcelona (ES); Santiago Nonell Marrugat, Sant Cugat del Vallés-Barcelona (ES); Francisco Marquillas Olondriz, Sant Cugat del Vallés-Barcelona (ES); Joan Sallares, Sant Cugat del Vallés-Barcelona (ES); Ricardo Miralles Bacete, Sant Cugat del Vallés-Barcelona (ES)

(73) Assignee: Interquim, S.A., Barcelona (ES)

( * ) Notice: Subject to any disclaimer, the term of this patent is extended or adjusted under 35 U.S.C. 154(b) by 0 days.

(21) Appl. No.: 13/501,848

(22) PCT Filed: Oct. 14, 2010

(86) PCT No.: PCT/EP2010/065454
§ 371 (c)(1),
(2), (4) Date: May 24, 2012

(87) PCT Pub. No.: WO2011/045389
PCT Pub. Date: Apr. 21, 2011

(65) Prior Publication Data
US 2012/0230932 A1    Sep. 13, 2012

(30) Foreign Application Priority Data

Oct. 15, 2009 (EP) .................................... 09173122

(51) Int. Cl.
*A61K 8/00* (2006.01)
*C07F 7/18* (2006.01)

(52) U.S. Cl.
CPC .................................... *C07F 7/1836* (2013.01)
USPC ............................................................ 424/60

(58) Field of Classification Search
None
See application file for complete search history.

(56) References Cited

U.S. PATENT DOCUMENTS 4,372,835 A    2/1983    Chung et al.

FOREIGN PATENT DOCUMENTS

WO    2006100225 A2    9/2006

OTHER PUBLICATIONS

International Search Report PCT/EP2010/065454 Date of mailing Dec. 1, 2011.
Russian Office Action (RuPTO) dated Aug. 27, 2014.

*Primary Examiner* — Michael G Hartley
*Assistant Examiner* — Robert Cabral
(74) *Attorney, Agent, or Firm* — Hoffmann & Baron, LLP

(57) ABSTRACT

The present invention relates to organosilicon polymers containing benzoic acid esters in form of particles, process for their preparation, cosmetic or dermatological composition comprising them, as well as their use for protecting a human or animal living body from UV radiation.

7 Claims, 12 Drawing Sheets

SILYL POLYMERIC BENZOIC ACID ESTER COMPOUNDS, USES, AND COMPOSITIONS THEREOF

CROSS-REFERENCE TO RELATED APPLICATIONS

This application is a 371 National Stage Filing, of PCT Application No. PCT/EP2010/065454, filed Oct. 14, 2010, which claims the benefit to European Application No. 09173122.4, filed Oct. 15, 2009, the contents of which are incorporated by reference herein.

TECHNICAL FIELD

This invention is directed to organosilicon polymers containing benzoic acid esters in form of particles to be used in topical preparations for affording protection against sunlight or other radiation.

BACKGROUND

There is a constantly increasing need for sunscreen protection agents in a population that is exposed to an increasing amount of damaging sunlight. The damage can be immediate and long-term, with effects ranging from sunburn, rashes, and cell and tissues damage to premature wrinkling and skin cancer. In this sense, many sunscreening chemicals have been developed in the past protecting against the harmful effect of UV-A and/or UV-B wavelength and even shorter wavelength. These chemicals are usually incorporated either alone or in combination with each other into cosmetic or pharmaceutical preparations which are widely known and used.

Most UV filters used in sunscreen compositions are monomeric compounds having the inherent risk that such compounds can penetrate the skin barrier, which is a highly undesirable effect. Thus, the major drawbacks derived from the use of common sunscreens are adverse reactions comprising cutaneous problems, such as allergic contact reactions, photocontact reactions, and drying or tightening of the skin. Subjective irritation associated with burning or stinging without objective erythema is the most common sensitivity complaint from sunscreens. This irritation is most frequently observed in the eye area. However, persistent objective irritant contact dermatitis is a more common side effect. Individuals with preexisting eczematous conditions have a significant predisposition to sensitization associated with their impaired cutaneous barrier. In addition, certain antibiotics, birth control pills, diuretics, antihistamines and antidepressants are among the commonly used drugs that can increase sensitivity to the sun's rays. Moreover, some of these cutaneous problems are induced by degradation products of the sunscreens formed upon exposure to sunlight.

Attempts have been made to solve the risk of skin penetration by encapsulating at least one type of UV filter which is present in a sunscreen formulation. For example, UV filters on the basis of polysiloxanes which may be either linear or cyclic have been described in WO93/04665, WO94/06404, EP538431, EP392883 and EP358584. With these polysiloxanes the risk of skin penetration is lower, but it is sometimes difficult to incorporate the polysiloxanes in sunscreen compositions due to incompatibility problems. Patent application WO2005/053631 refers to microcapsules with UV filter activity, wherein at least one type of crosslinkable chromophore with UV-A and/or UV-B and/or UV-C filter activity, and optionally at least one type of crosslinkable monomer which has no UV-A and/or UV-B and/or UV-C filter activity, are subjected to a crosslinking reaction in the absence of non-crosslinkable chromophores with UV-A and/or UV-B and/or UV-C filter activity. The invention also refers to sunscreen compositions comprising said microcapsules.

The prior art also describes some UV absorbers in the form of particles. In this sense, patent application WO2005/120440 refers to particles comprising an inorganic network and organic compounds covalently bonded to the network via a spacer group, characterised in that the organic compounds are present in the interior of the particles and optionally also on the surface of the particles. The invention also refers to formulations and compositions comprising said particles.

Patent application WO2009/101016 and Walenzyk, T. et al., *International Journal of Cosmetic Science* (2005), 27(3), 177-189, refer to particles that can be obtained by the reaction of inorganic nanoparticles with organic molecules containing functional groups, and use thereof as UV absorbers in cosmetic or dermatological applications.

Some benzoic acid ester compounds have been discovered and disclosed in WO2006100225, as well as their uses as photochemical precursors of ultraviolet absorbers, processes, cosmetic or pharmaceutical compositions, personal care compositions, and industrial compositions related thereto. Some silane-functionalized ultraviolet screening agent precursors have also been disclosed in U.S. Pat. No. 4,328,346. These compounds undergo a photochemical transformation in the presence of sunlight that enhances their UV screening ability. However, it is still desired to develop new sunscreen compounds with high purity, a lower risk of side effects, increased photostability and increased persistence on the skin.

BRIEF DESCRIPTION OF THE INVENTION

The present invention discloses silyl polymeric benzoic acid ester compounds useful as progressive photoprotective agents over UV radiation. An advantage conferred by these compounds over those described in the prior art is that they exhibit a micro- or nanoparticle form, wherein the particles, in addition to be homogenous and spherical or quasi spherical, have the relevant physical property of being essentially hermetic. Hermeticism avoids the release of the benzoic acid ester compounds and its phototransformation products. As such, they are endowed with a safer profile both for the sunscreen user and for the environment.

The polymers of the present invention also show a progressive UV protection depending on the time to sun exposition and the degree of sun radiation. Thus, compositions containing such compounds constitute a safer method to take sunbaths than conventional sunscreen products, since protection increases with time of sun exposition and the intensity of radiation.

The polymers of the invention exhibit ultraviolet absorbing properties per se and are susceptible to be photochemically converted in situ to another screen compound with a higher UV protection.

In a first aspect, the present invention refers to a process for the preparation of an organosilicon progressive photoprotective polymer, which comprises the reaction of a monomer of formula (I):

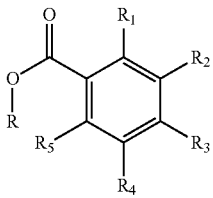

wherein:
R is selected from the group consisting of (i), (ii), (iii), and (iv):

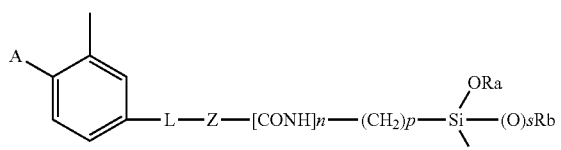

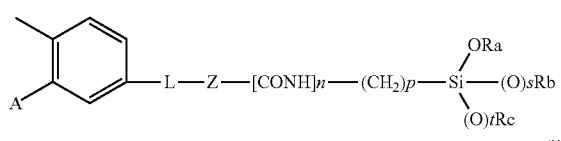

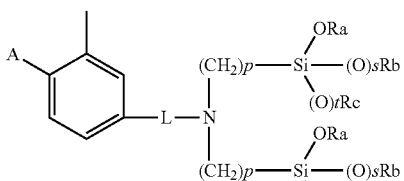

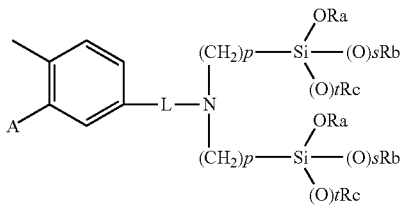

wherein:
$R_1$, $R_2$, $R_3$, $R_4$ and $R_5$ are independently selected from the group consisting of H, linear or branched $(C_1-C_6)$alkyl, $(C_3-C_6)$cycloalkyl, $OR_6$, $NH_2$, $NHR_7$, $NR_8R_9$, COOH, $COOR_{10}$, $CONH_2$, $CONHR_{11}$, $CONR_{12}R_{13}$, $SO_2NH_2$, $SO_2NHR_{14}$, and $SO_2NR_{15}R_{16}$;

$R_6$ is linear or branched $(C_1-C_6)$alkyl or $(C_3-C_6)$cycloalkyl;
$R_7$ is linear or branched $(C_1-C_6)$alkyl or $(C_3-C_6)$cycloalkyl;
$R_8$ is linear or branched $(C_1-C_6)$alkyl or $(C_3-C_6)$cycloalkyl;
$R_9$ is linear or branched $(C_1-C_6)$alkyl or $(C_3-C_6)$cycloalkyl; or $R_8$ and $R_9$ taken together with the nitrogen atom to which they are attached form a pyrrolidine, piperidine or morpholine ring;

$R_{10}$ is linear or branched $(C_1-C_6)$alkyl or $(C_3-C_6)$cycloalkyl;
$R_{11}$ is linear or branched $(C_1-C_6)$alkyl or $(C_3-C_6)$cycloalkyl;
$R_{12}$ is linear or branched $(C_1-C_6)$alkyl or $(C_3-C_6)$cycloalkyl;
$R_{13}$ is linear or branched $(C_1-C_6)$alkyl or $(C_3-C_6)$cycloalkyl; or $R_{12}$ and $R_{13}$ taken together with the nitrogen atom to which they are attached form a pyrrolidine, piperidine or morpholine ring;

$R_{14}$ is linear or branched $(C_1-C_6)$alkyl or $(C_3-C_6)$cycloalkyl;
$R_{15}$ is linear or branched $(C_1-C_6)$alkyl or $(C_3-C_6)$cycloalkyl;
$R_{16}$ is linear or branched $(C_1-C_6)$alkyl or $(C_3-C_6)$cycloalkyl; or $R_{15}$ and $R_{16}$ taken together with the nitrogen atom to which they are attached form a pyrrolidine, piperidine or morpholine ring;

A is H, linear or branched $(C_1-C_6)$alkyl, $(C_3-C_6)$cycloalkyl, $OR'_1$, $NH_2$, $NHR'_2$ or $NR'_3R'_4$;
L is a single bond, —$CH_2$—, or —$CH_2$—$CH(R_L)$—
Z is NH or O;
Ra is linear or branched $(C_1-C_6)$alkyl, linear or branched $(C_2-C_6)$alkenyl, $(C_3-C_6)$cycloalkyl or phenyl;
Rb is linear or branched $(C_1-C_6)$alkyl, linear or branched $(C_2-C_6)$alkenyl, $(C_3-C_6)$cycloalkyl or phenyl;
Rc is linear or branched $(C_1-C_6)$alkyl, linear or branched $(C_2-C_6)$alkenyl, $(C_3-C_6)$cycloalkyl or phenyl;
$R'_1$ is linear or branched $(C_1-C_6)$alkyl or $(C_3-C_6)$cycloalkyl;
$R'_2$ is linear or branched $(C_1-C_6)$alkyl or $(C_3-C_6)$cycloalkyl;
$R'_3$ is linear or branched $(C_1-C_6)$alkyl or $(C_3-C_6)$cycloalkyl;
$R'_4$ is linear or branched $(C_1-C_6)$alkyl or $(C_3-C_6)$cycloalkyl; or $R'_3$ and $R'_4$ taken together with the nitrogen atom to which they are attached form a pyrrolidine, piperidine or morpholine ring;
$R_L$ is H, linear or branched $(C_1-C_6)$alkyl or $(C_3-C_6)$cycloalkyl;
n is an integer selected from 0 and 1;
p is an integer selected from 2, 3 and 4;
s is an integer selected from 0 and 1;
t is an integer selected from 0 and 1;
with a compound of formula (IV):

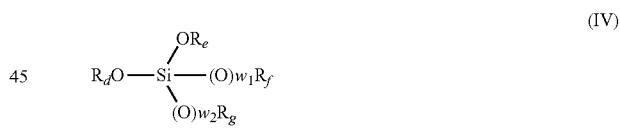

wherein:
Rd is a linear or branched $(C_1-C_6)$alkyl;
Re, Rf and Rg are independently a linear or branched $(C_1-C_6)$alkyl, linear or branched $(C_2-C_6)$alkenyl, $(C_3-C_6)$cycloalkyl or phenyl,
$w_1$ and $w_2$ are independently 0 or 1,
in an alkanol/water mixture.

In a second aspect, the present invention refers to an organosilicon progressive photoprotective polymer obtainable by a process as defined above, characterised in that it exhibits a micro- or nanoparticle form.

In a third aspect, the present invention refers to the use of an organosilicon progressive photoprotective polymer as defined above, in the preparation of a cosmetic or dermatological composition for protecting a human or animal living body from UV radiation.

In a fourth aspect, the present invention refers to the use of a photoprotective polymer as defined above as photochemical precursor of UV absorbers.

In a fifth aspect, the present invention refers to the use of a photoprotective polymer as defined above, in the preparation of a cosmetic or dermatological composition to be applied to human or animal living body, characterized by a progressive UV protection depending on the time to sun exposition and the degree of sun radiation.

In a sixth aspect, the present invention refers to a photoprotective polymer as defined above, for its use in protecting a human or animal living body from UV radiation.

In a seventh aspect, the present invention refers to a cosmetic or dermatological composition comprising an organosilicon progressive photoprotective polymer as defined above.

In an eight aspect, the present invention refers to a monomer of formula (I):

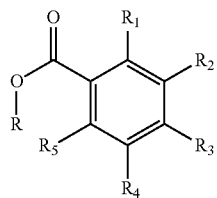

(I)

wherein:

R is selected from the group consisting of (i), (ii), (iii), and (iv):

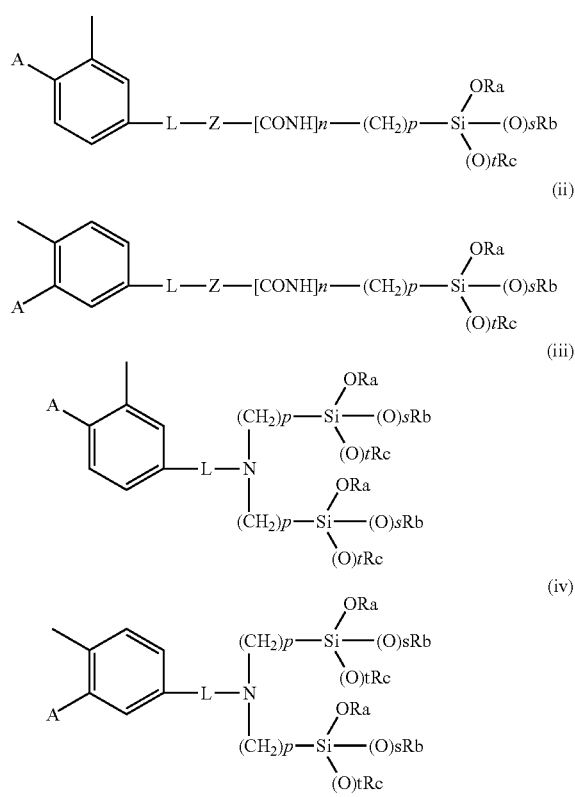

$R_1$, $R_2$, $R_3$, $R_4$ and $R_5$ are independently selected from the group consisting of H, linear or branched $(C_1-C_6)$alkyl, $(C_3-C_6)$cycloalkyl, $OR_6$, $NH_2$, $NHR_7$, $NR_8R_9$, $COOH$, $COOR_{10}$, $CONH_2$, $CONHR_{11}$, $CONR_{12}R_{13}$, $SO_2NH_2$, $SO_2NHR_{14}$, and $SO_2NR_{15}R_{16}$;

$R_6$ is linear or branched $(C_1-C_6)$alkyl or $(C_3-C_6)$cycloalkyl;
$R_7$ is linear or branched $(C_1-C_6)$alkyl or $(C_3-C_6)$cycloalkyl;
$R_8$ is linear or branched $(C_1-C_6)$alkyl or $(C_3-C_6)$cycloalkyl;
$R_9$ is linear or branched $(C_1-C_6)$alkyl or $(C_3-C_6)$cycloalkyl; or $R_8$ and $R_9$ taken together with the nitrogen atom to which they are attached form a pyrrolidine, piperidine or morpholine ring;
$R_{10}$ is linear or branched $(C_1-C_6)$alkyl or $(C_3-C_6)$cycloalkyl;
$R_{11}$ is linear or branched $(C_1-C_6)$alkyl or $(C_3-C_6)$cycloalkyl;
$R_{12}$ is linear or branched $(C_1-C_6)$alkyl or $(C_3-C_6)$cycloalkyl;
$R_{13}$ is linear or branched $(C_1-C_6)$alkyl or $(C_3-C_6)$cycloalkyl; or $R_{12}$ and $R_{13}$ taken together with the nitrogen atom to which they are attached form a pyrrolidine, piperidine or morpholine ring;
$R_{14}$ is linear or branched $(C_1-C_6)$alkyl or $(C_3-C_6)$cycloalkyl;
$R_{15}$ is linear or branched $(C_1-C_6)$alkyl or $(C_3-C_6)$cycloalkyl;
$R_{16}$ is linear or branched $(C_1-C_6)$alkyl or $(C_3-C_6)$cycloalkyl; or $R_{15}$ and $R_{16}$ taken together with the nitrogen atom to which they are attached form a pyrrolidine, piperidine or morpholine ring;
A is H, linear or branched $(C_1-C_6)$alkyl, $(C_3-C_6)$cycloalkyl, $OR'_1$, $NH_2$, $NHR'_2$ or $NR'_3R'_4$;
L is a single bond, $-CH_2-$, or $-CH_2-CH(R_L)-$
Z is NH or O;
Ra is linear or branched $(C_1-C_6)$alkyl, linear or branched $(C_2-C_6)$alkenyl, $(C_3-C_6)$cycloalkyl or phenyl;
Rb is linear or branched $(C_1-C_6)$alkyl, linear or branched $(C_2-C_6)$alkenyl, $(C_3-C_6)$cycloalkyl or phenyl;
Rc is linear or branched $(C_1-C_6)$alkyl, linear or branched $(C_2-C_6)$alkenyl, $(C_3-C_6)$cycloalkyl or phenyl;
$R'_1$ is linear or branched $(C_1-C_6)$alkyl or $(C_3-C_6)$cycloalkyl;
$R'_2$ is linear or branched $(C_1-C_6)$alkyl or $(C_3-C_6)$cycloalkyl;
$R'_3$ is linear or branched $(C_1-C_6)$alkyl or $(C_3-C_6)$cycloalkyl;
$R'_4$ is linear or branched $(C_1-C_6)$alkyl or $(C_3-C_6)$cycloalkyl; or $R'_3$ and $R'_4$ taken together with the nitrogen atom to which they are attached form a pyrrolidine, piperidine or morpholine ring;
$R_L$ is H, linear or branched $(C_1-C_6)$alkyl or $(C_3-C_6)$cycloalkyl;
n is an integer selected from 0 and 1;
p is an integer selected from 2, 3 and 4;
s is an integer selected from 0 and 1;
t is an integer selected from 0 and 1;
or enantiomeric forms, or cosmetically or dermatologically acceptable salts thereof, with the proviso that when R is (i), then A, L, Z, n, p, s, t, and $R_1$-$R_5$ cannot be at the same time H, single bond, O, 0, 3, 1, 1, and all H respectively.

In a ninth aspect, the present invention relates to a process for the preparation of a monomer of formula (I) as defined above when R is a group (i) or (ii), which comprises the reaction of a compound of formula (II'):

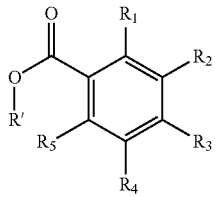
(II')

wherein:
R' is a group (i') or (ii'):

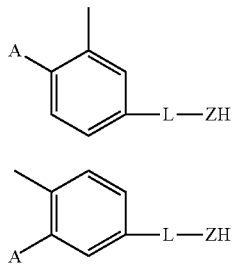
(i')
(ii')

and $R_1$-$R_5$, A, L and Z are as defined above, with a compound of formula (III')

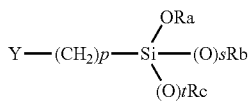
(III')

wherein:
Y is selected from the group consisting of Cl, Br, I, and O=C=N, and
p, s, t, Ra, Rb, and Rc are as defined above, wherein the (II') to (III') molar ratio is in the range from 1:1 to 1:2.

In an tenth aspect, the present invention relates to a process for the preparation of a monomer of formula (I) as defined above, when R is a group (iii) or (iv), which comprises the reaction of a compound of formula (II"):

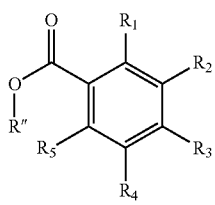
(II")

wherein:
R" is a group (iii") or (iv"):

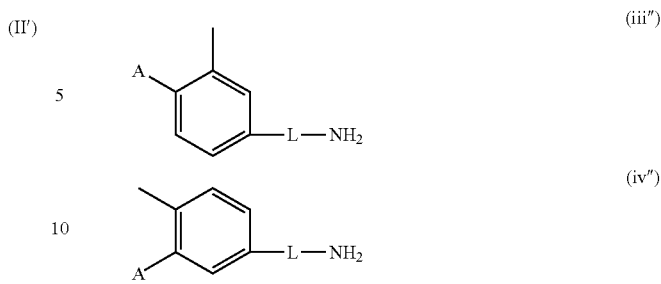
(iii")
(iv")

and $R_1$-$R_5$, A, and L are is as defined above, with a compound of formula (III"):

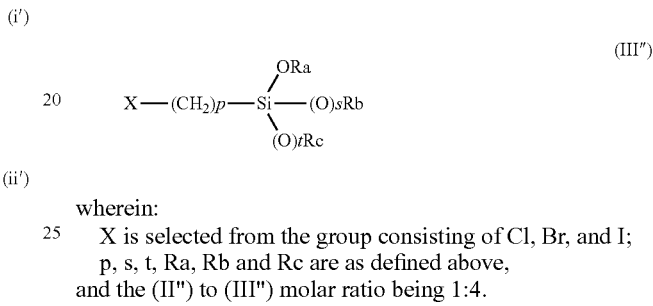
(III")

wherein:
X is selected from the group consisting of Cl, Br, and I;
p, s, t, Ra, Rb and Rc are as defined above,
and the (II") to (III") molar ratio being 1:4.

Figure 1:
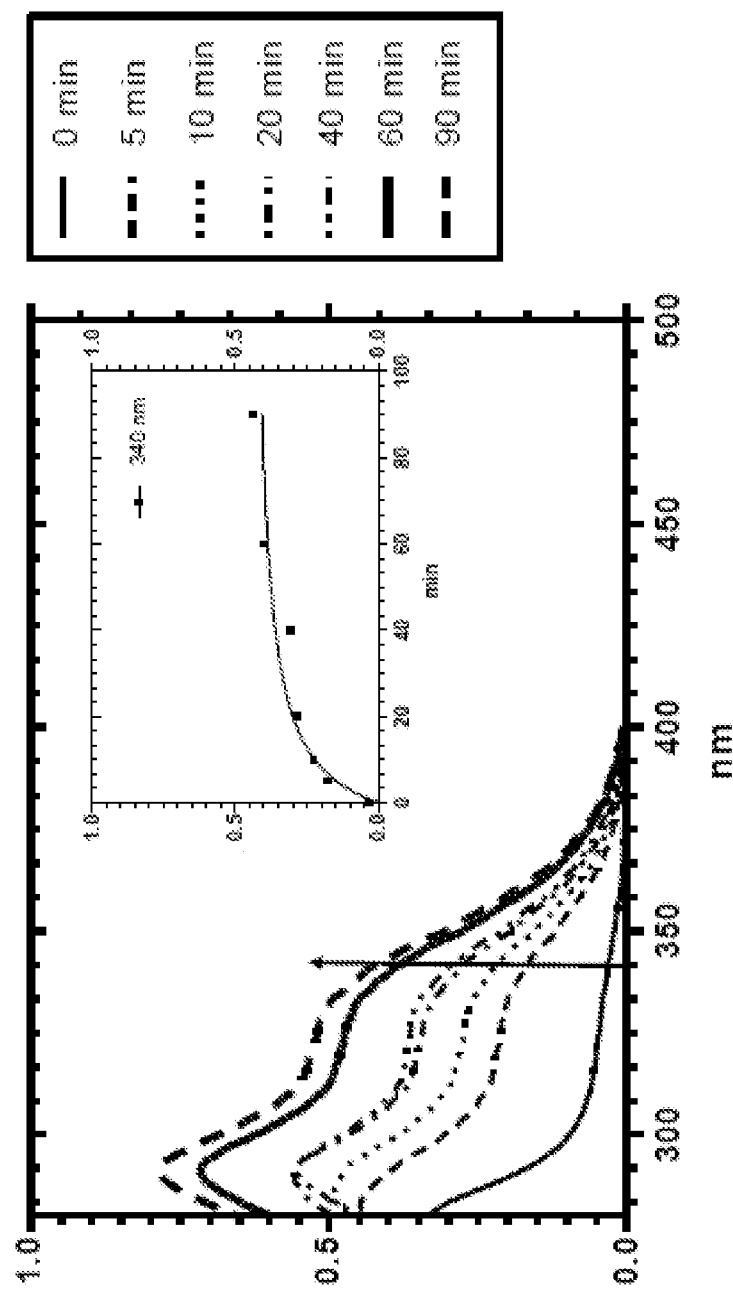
FIG. 1 shows the UV-Vis spectrum of 3-(3-(triethoxysilyl)propoxy)phenyl benzoate particles.
Figure 2:
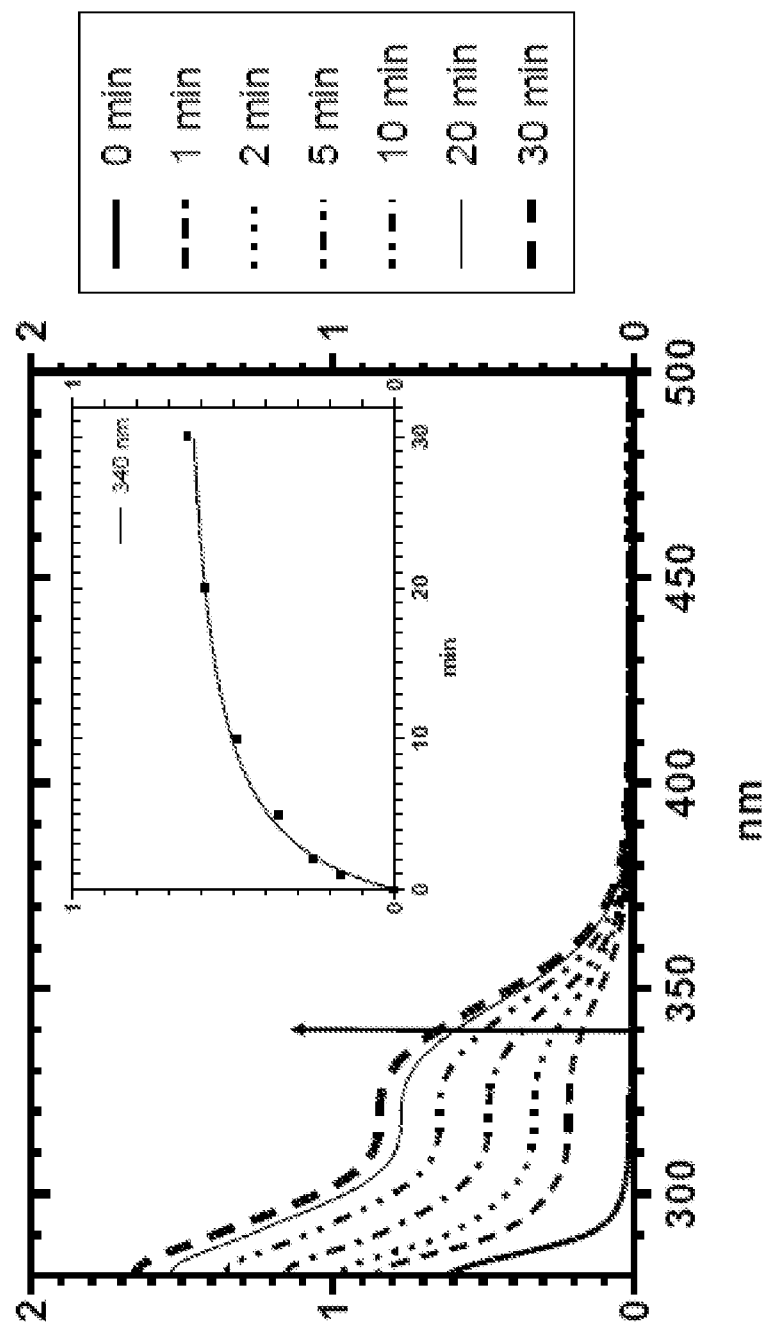
FIG. 2 shows the UV-Vis spectrum of 3-(3-triethoxysilyl)propylcarbamoyloxy)phenyl benzoate particles.
Figure 3:
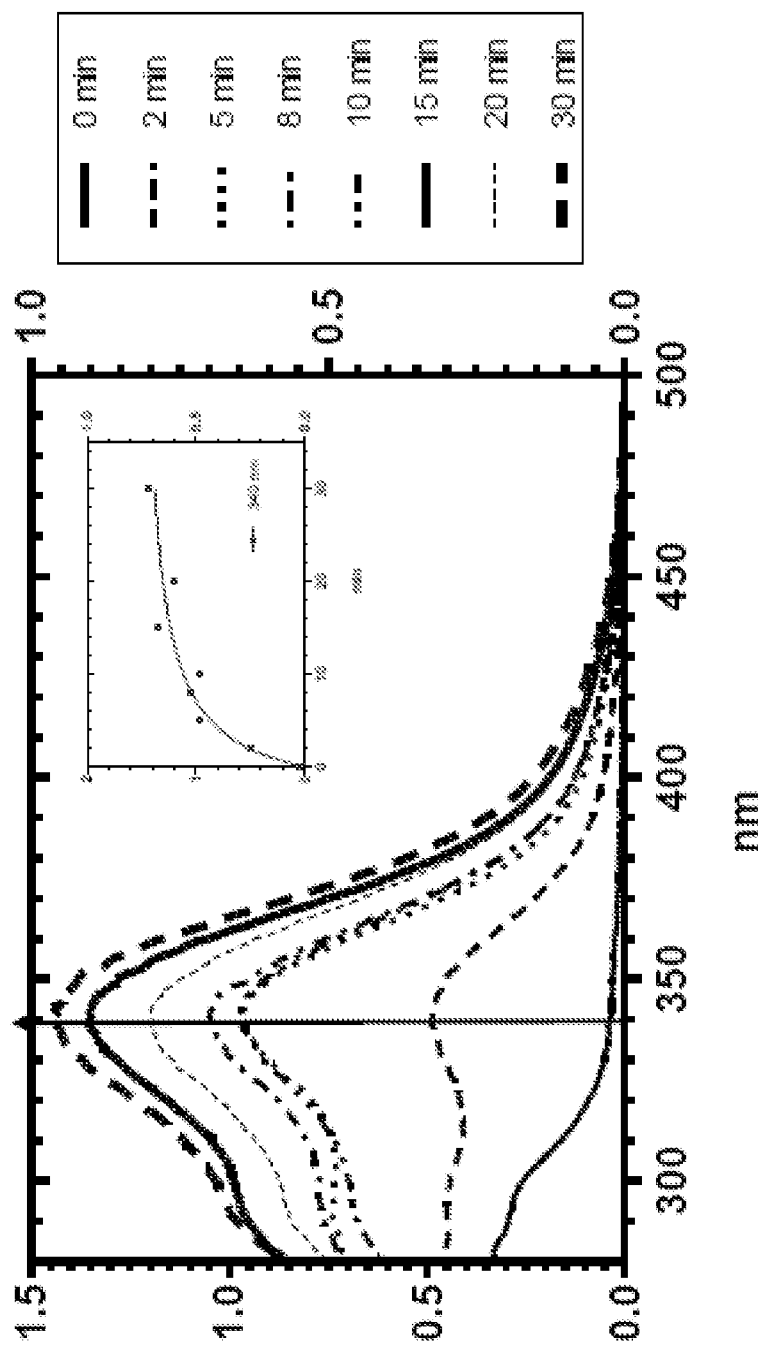
FIG. 3 shows the UV-Vis spectrum of 3-(3-triethoxysilyl)propylamino)phenyl benzoate particles.
Figure 4:
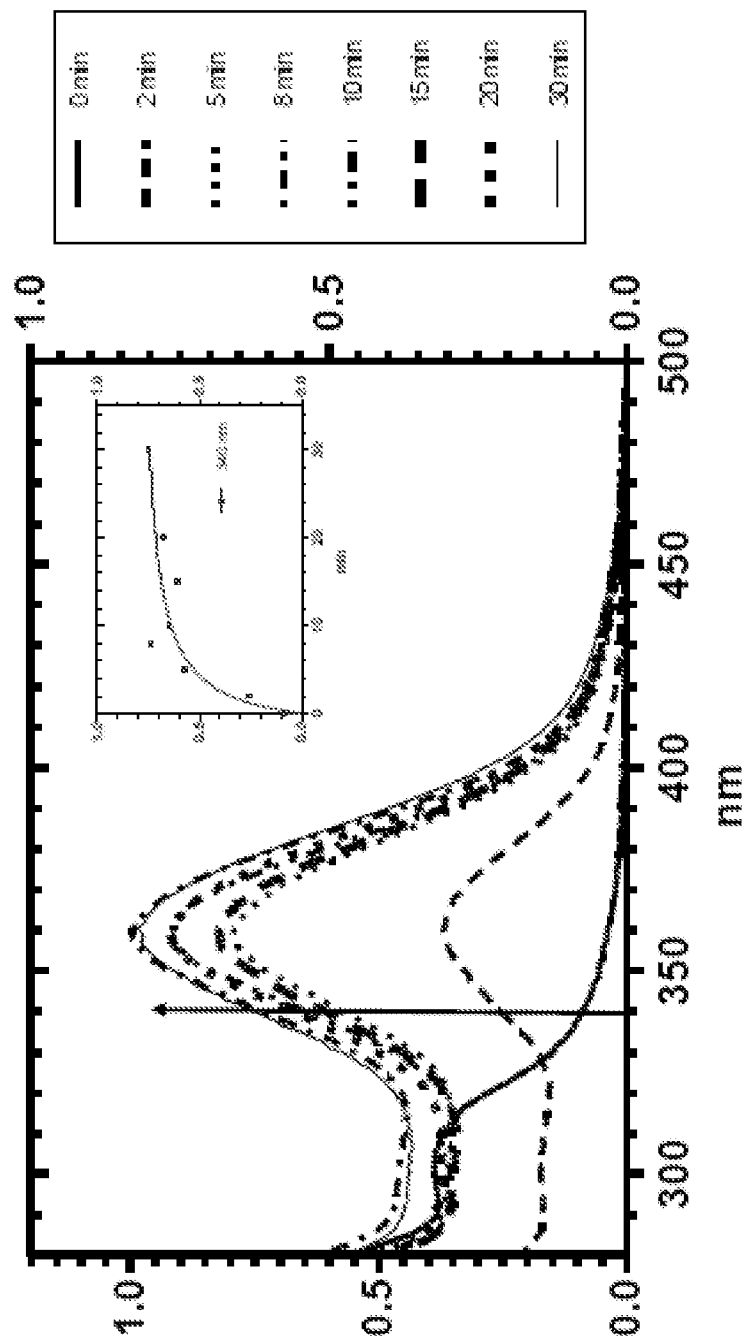
FIG. 4 shows the UV-Vis spectrum of 3-(bis(3-(triethoxysilyl)propyl)aminophenyl benzoate particles.
Figure 5:
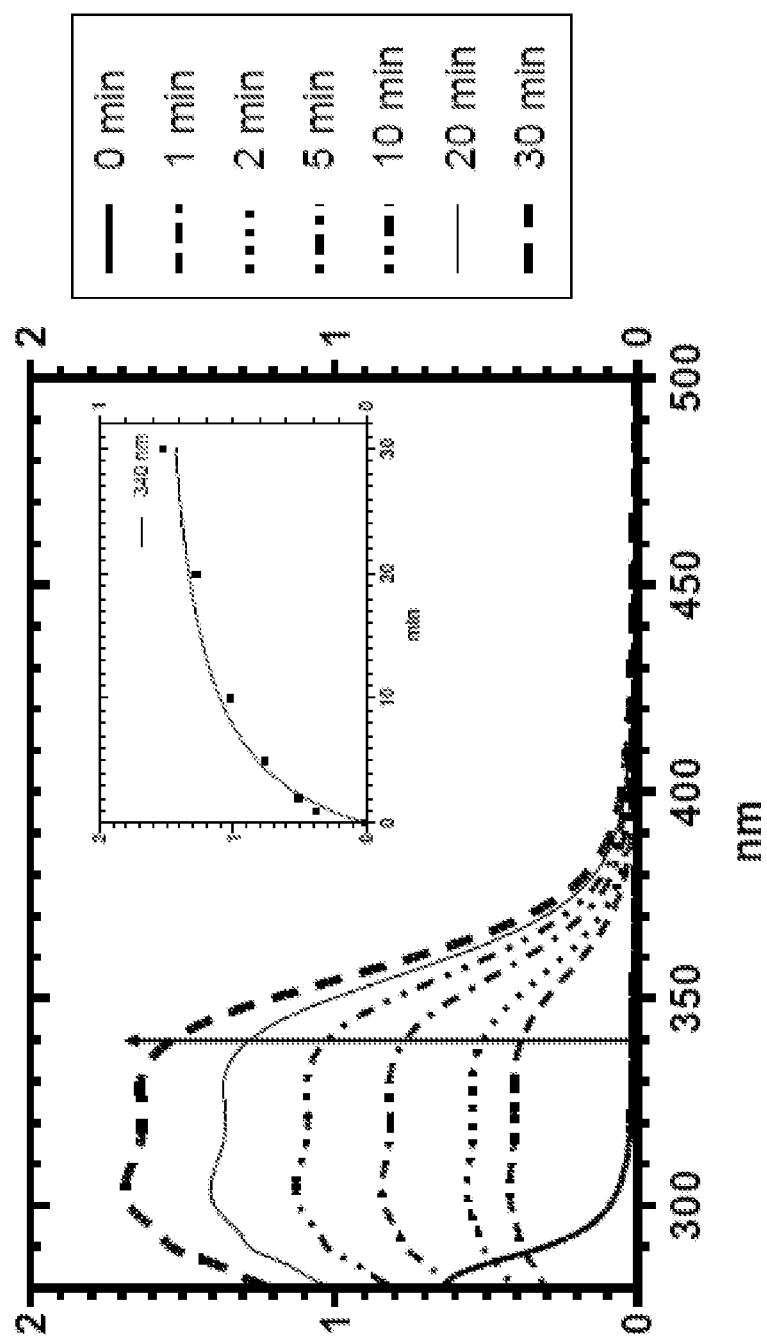
FIG. 5 shows the UV-Vis spectrum of 3-(3-(3-triethoxysilyl)propyl)ureido)phenyl benzoate particles.
Figure 6:
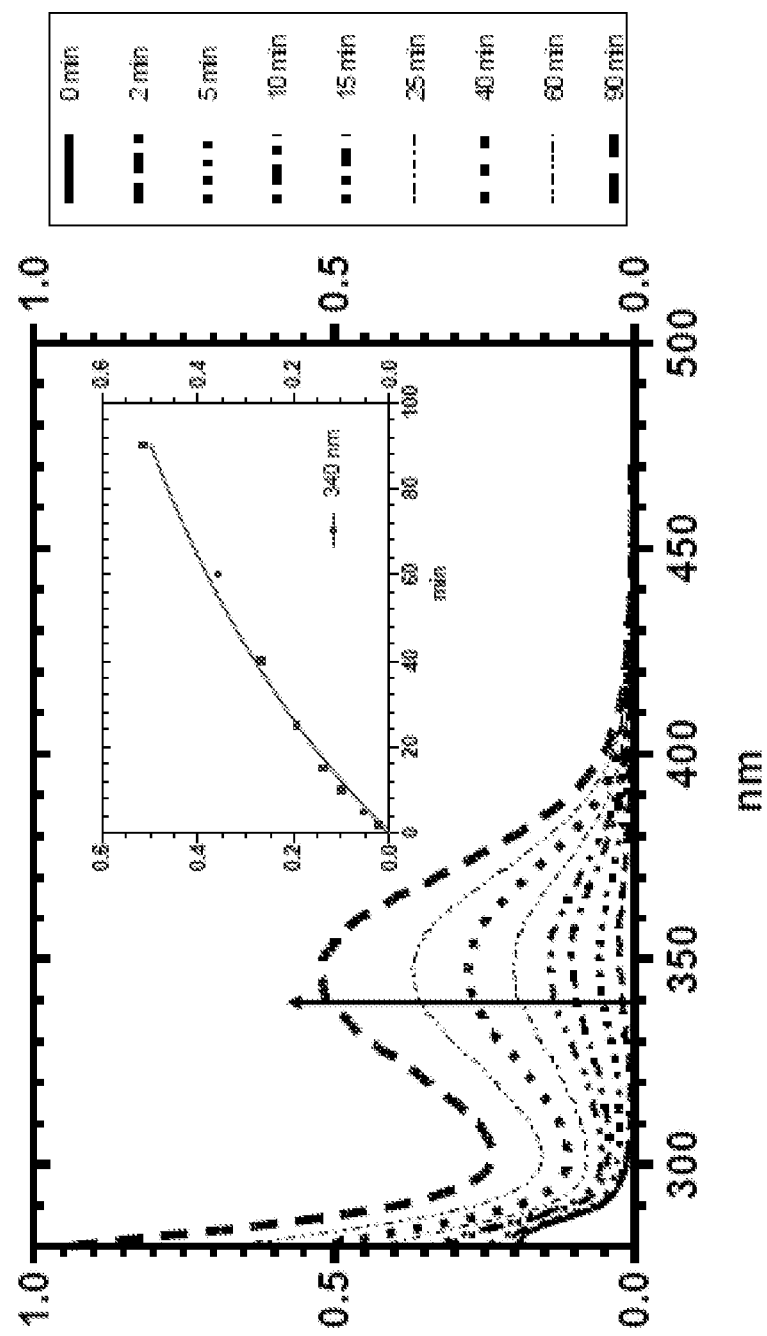
FIG. 6 shows the UV-Vis spectrum of 4-((3-(triethoxysilyl)propoxy)methyl)phenyl benzoate particles.
Figure 7:
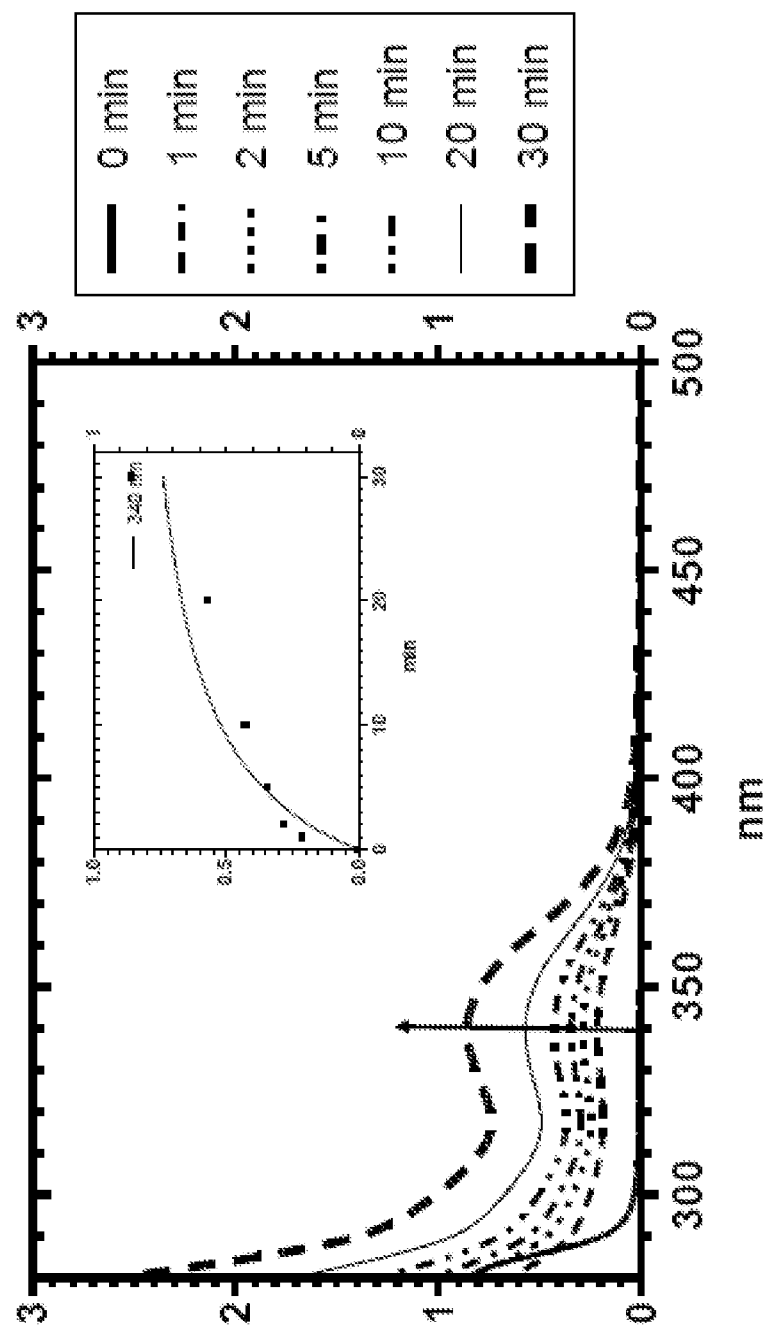
FIG. 7 shows the UV-Vis spectrum of 4-((3-(triethoxysilyl)propylcarbamoyloxy)methyl)phenyl benzoate particles.
Figure 8:
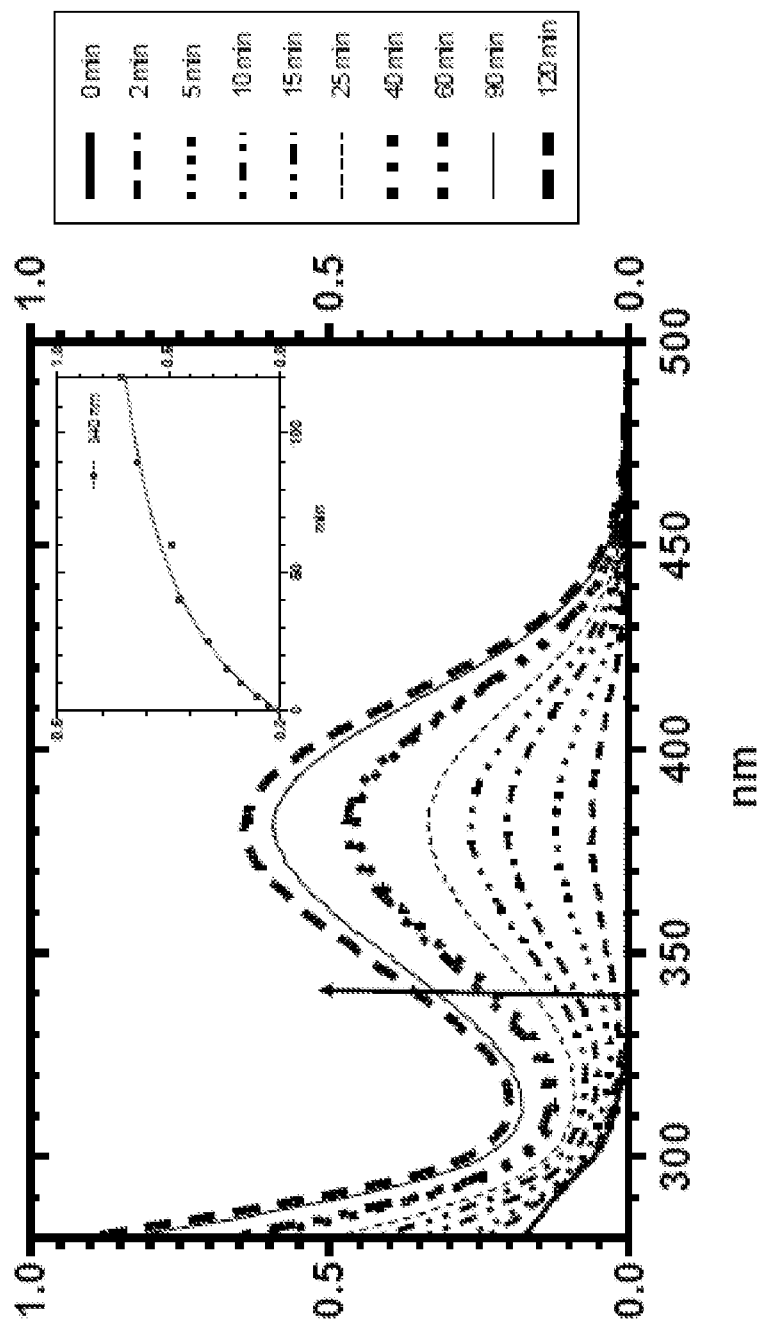
FIG. 8 shows the UV-Vis spectrum of 4-(3-(triethoxysilyl)propoxy)phenyl benzoate particles.
Figure 9:
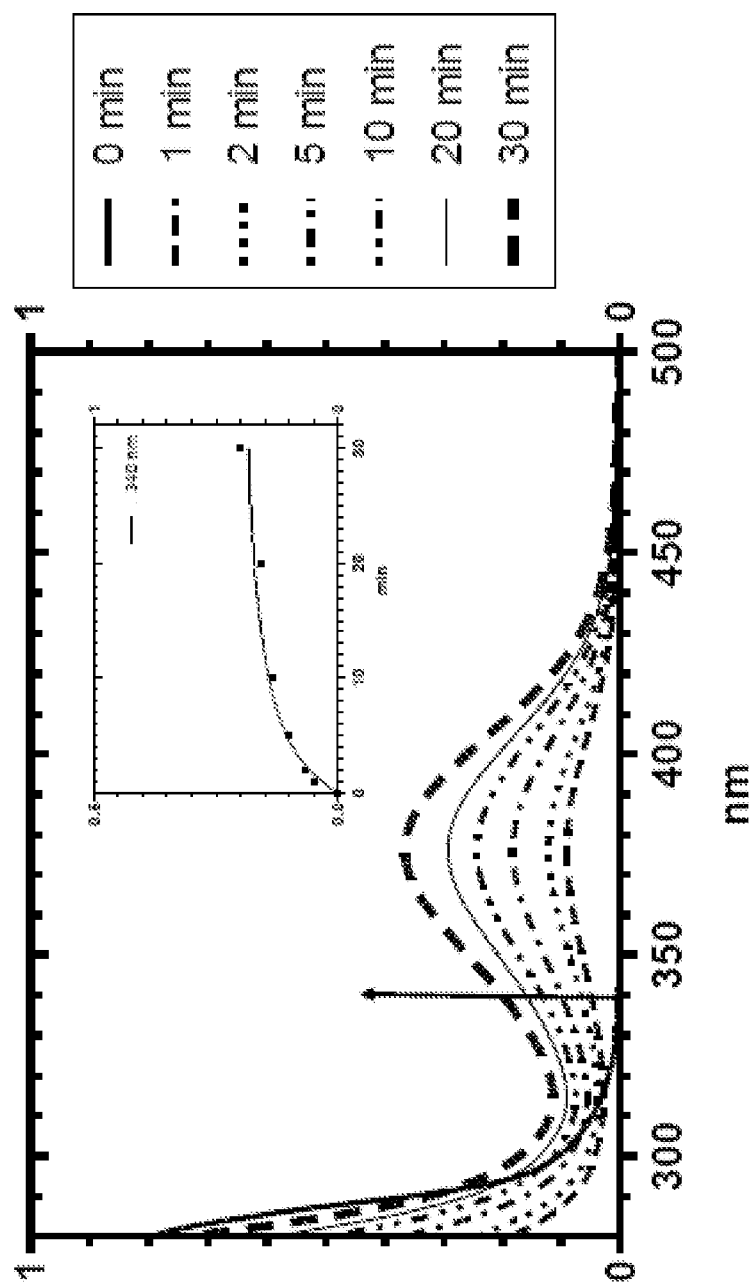
FIG. 9 shows the UV-Vis spectrum of 4-(3-(triethoxysilyl)propylcarbamoyloxy)phenyl benzoate particles.
Figure 10:
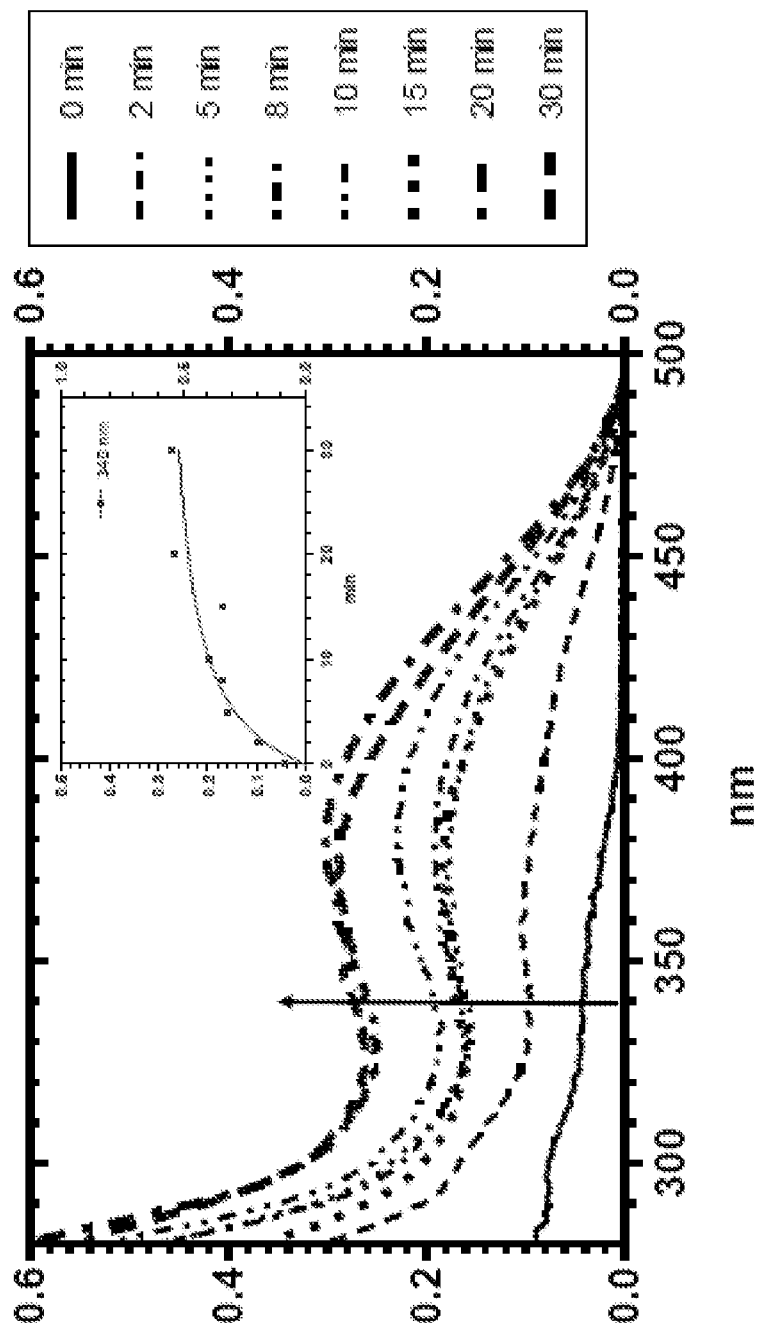
FIG. 10 shows the UV-Vis spectrum of 4-(3-(triethoxysilyl)propylamino)phenyl benzoate particles.
Figure 11:
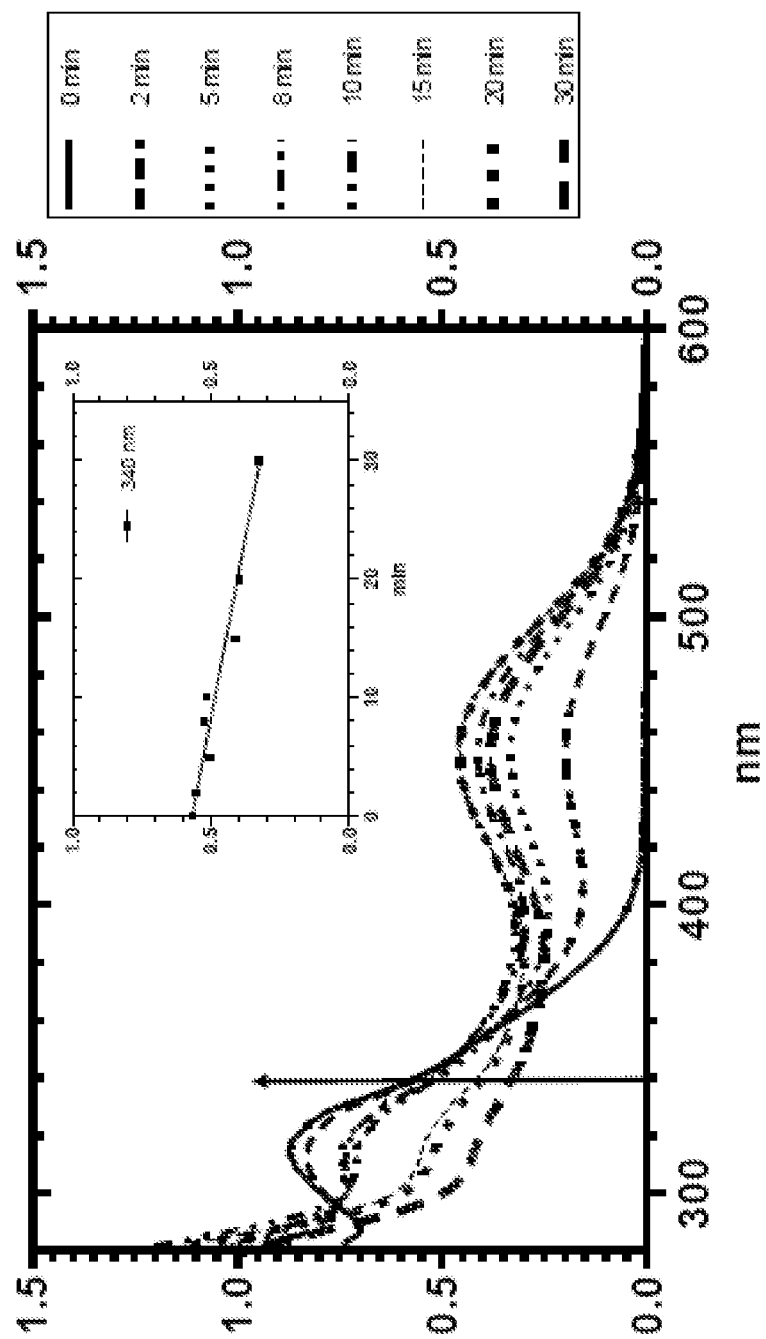
FIG. 11 shows the UV-Vis spectrum of 4-(bis(3-(triethoxysilyl)propylamino)phenyl benzoate particles.
Figure 12:
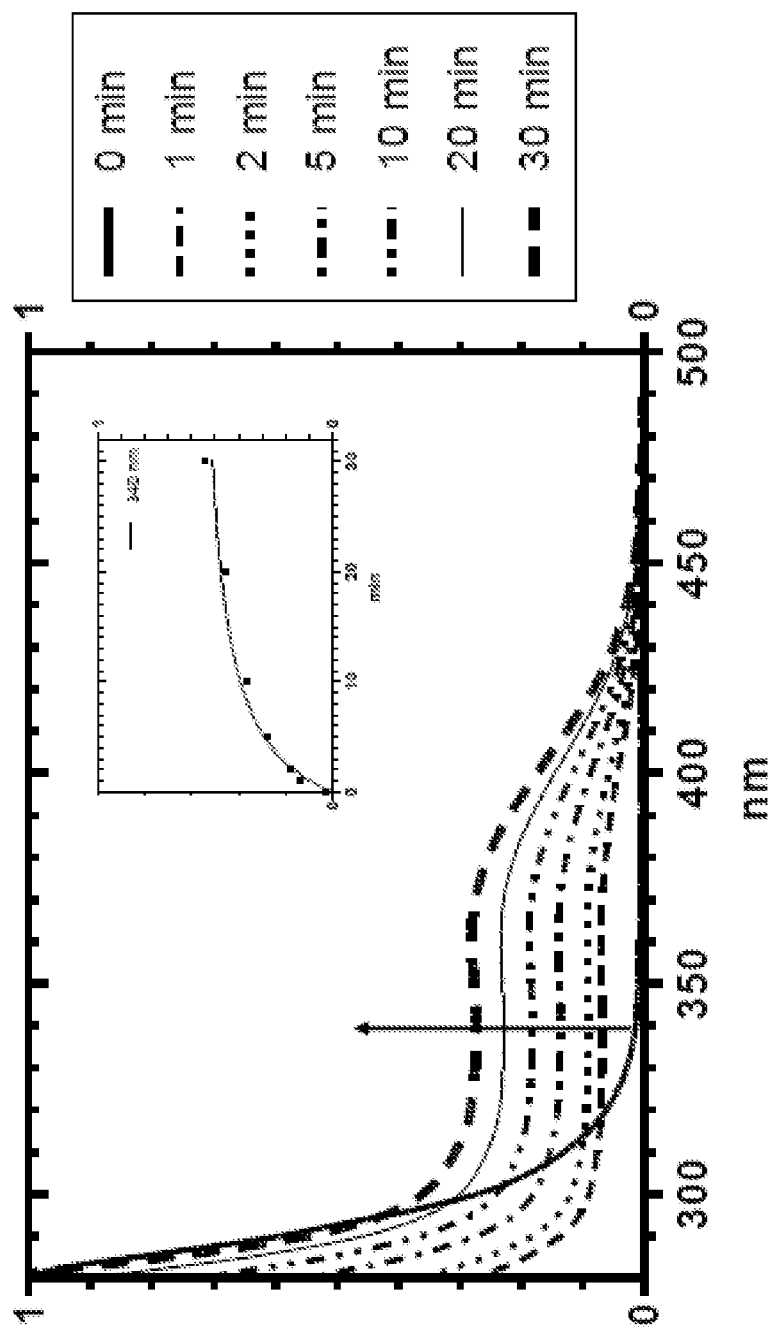
FIG. 12 shows the UV-Vis spectrum of 4-(3-(3-(triethoxysilyl)propyl)ureido)phenyl benzoate particles.

In all figures the axis of ordinates represents absorbance, and the axis of abscises represents wavelength in nm. Small drawings in the figures depict absorbance kinetics measurements at 340 nm.

DETAILED DESCRIPTION OF THE INVENTION

In the context of the present invention, the following terms have the meaning detailed below.
"$C_1$-$C_6$ alkyl" refers to a linear or branched hydrocarbon chain radical consisting of 1 to 6 carbons, containing no unsaturation, and which is attached to the rest of the molecule by a single bond, e.g., methyl, ethyl, 1-propyl, 2-propyl, 1-butyl, t-butyl, 1-pentyl, etc. Alkyl radicals may be optionally substituted by one or more substituents such as aryl, halo, hydroxy, alkoxy, carboxy, cyano, carbonyl, acyl, amino, nitro, mercapto, alkylthio, etc, provided that they do not affect the polymerization process.

"$C_2$-$C_6$ alkenyl" refers to an alkyl radical as defined above consisting of 2 to 6 carbons and having one or more unsaturated bonds.

"$C_3$-$C_6$ cycloalkyl" refers to a stable 3- to 6-membered monocyclic radical which is saturated or partially saturated, and which consist solely of carbon and hydrogen atoms, such as cyclohexyl or adamantyl. Cycloalkyl radicals may be optionally substituted by one or more substituents such as alkyl, halo, hydroxy, amino, cyano, nitro, alkoxy, carboxy, etc, provided that they do not affect the polymerization process.

The term "alkanol" refers to a linear or branched hydrocarbon chain radical having 1 to 6 carbon atoms and containing a hydroxyl group.

The term "cosmetically or dermatologically acceptable salts" in the context of this invention must be understood as any salt that is tolerated physiologically (normally meaning that it is not toxic, particularly, as a result of the counter-ion) when applied or used, particularly, in humans and/or mammals. Examples of these salts include acid addition salts and alkali addition salts. Acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

In a first aspect, the present invention refers to a process (from now onwards process 1) for the preparation of an organosilicon progressive photoprotective polymer, which comprises the reaction of a monomer of formula (I) as defined above with a compound of formula (IV) as defined above in an alkanol/water mixture.

In a preferred embodiment, in the monomer of formula (I) used in the process 1 of the invention $R_1$, $R_2$, $R_3$, $R_4$ and $R_5$ are H and p is 3.

In another preferred embodiment, in the monomer of formula (I) used in the process 1 of the invention R is (i) or (ii); Ra is a linear ($C_1$-$C_6$)alkyl; Rb is a linear ($C_1$-$C_6$)alkyl; and Rc is a linear ($C_1$-$C_6$)alkyl. Even more preferably, R is (i) or (ii); $R_1$, $R_2$, $R_3$, $R_4$ and $R_5$ are H; p is 3; Ra is a linear ($C_1$-$C_6$)alkyl; Rb is a linear ($C_1$-$C_6$)alkyl; and Rc is a linear ($C_1$-$C_6$)alkyl.

In another preferred embodiment, in the monomer of formula (I) used in the process 1 of the invention R is (iii) or (iv), Ra is a linear ($C_1$-$C_6$)alkyl, Rb is a linear ($C_1$-$C_6$)alkyl, and Rc is a linear ($C_1$-$C_6$)alkyl. Even more preferably, R is (iii) or (iv); $R_1$, $R_2$, $R_3$, $R_4$ and $R_5$ are H; p is 3; Ra is a linear ($C_1$-$C_6$)alkyl; Rb is a linear ($C_1$-$C_6$)alkyl; and Rc is a linear ($C_1$-$C_6$)alkyl.

In another preferred embodiment, the monomer of formula (I) used in the process 1 of the invention is selected from the group consisting of:
3-(3-(triethoxysilyl)propoxy)phenyl benzoate;
3-(3-(triethoxysilyl)propylcarbamoyloxy)phenyl benzoate;
3-(3-(triethoxysilyl)propylamino)phenyl benzoate;
3-(bis(3-(triethoxysilyl)propyl)amino)phenyl benzoate;
3-(3-(3-(triethoxysilyl)propyl)ureido)phenyl benzoate;
4-((3-(triethoxysilyl)propoxy)methyl)phenyl benzoate;
4-((3-(triethoxysilyl)propylcarbamoyloxy)methyl)phenyl benzoate;
4-(3-(triethoxysilyl)propoxy)phenyl benzoate;
4-(3-(triethoxysilyl)propylcarbamoyloxy)phenyl benzoate;
4-(3-(triethoxysilyl)propylamino)phenyl benzoate;
4-(bis(3-(triethoxysilyl)propyl)amino)phenyl benzoate; and
4-(3-(3-(triethoxysilyl)propyl)ureido)phenyl benzoate.

In a particular embodiment of the invention, process 1 is carried out in the presence of a nitrogen-containing basic compound selected from the group consisting of ammonia, mono-alkylamine, di-alkylamine, tri-alkylamine, mono-alkanolamine, di-alkanolamine and tri-alkanolamine. Both alkyl and alkanol groups are linear or branched, having 1 to 6 carbon atoms. Preferably, the nitrogen-containing basic compound is ammonia.

In a second aspect, the present invention relates to an organosilicon progressive photoprotective polymer obtainable by process 1 of the invention.

The photoprotective polymers of the present invention obtainable as shown in this specification exhibit a micro- or nanoparticle form. Moreover, such particles have homogenous and spherical or quasi spherical form and are essentially hermetic.

In the context of the present invention, by the term "micro- or nano-particle form" it is understood particles having an average size lower than 100 microns. Usually, said particles have an average size ranging from 10 nm to 10 microns, preferably form 100 to 1500 nm.

The preparation of the particles by the process 1 of the invention has the advantage that the product can be obtained in the form of a suspension containing about 1 to 25% solids consisting of the hermetic spherical or quasi spherical particles which can directly be used in cosmetic or dermatological compositions of the present invention. As mentioned before, the hermetism is a relevant physical property of the polymers of the invention since the release of benzoic acid esters or their phototransformation products is minimised.

The photoprotective activity is due to in situ conversion to sunscreen 2-hydroxybenzophenone polymers through a photo-Fries rearrangement of the benzoic acid ester fragment to a 2-hydroxybenzophenone fragment as shown in Scheme 1 for illustrative purposes:

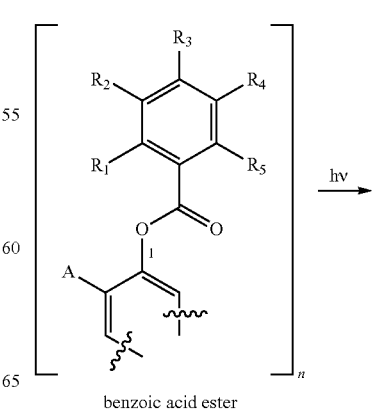

benzoic acid ester

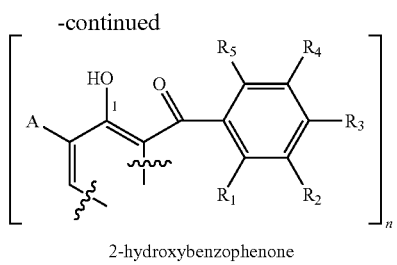

2-hydroxybenzophenone wherein $R_1$-$R_5$ and A are as defined above, and n is the number of monomeric units constituting the polymer.

These photoprotective polymers show a progressive UV protection depending on the time of sun exposure and the dose of sun radiation absorbed by the polymer. This progressive UV protection property is evidenced in their UVB and UVA screening ability. The extent of photo-Fries rearrangement is indicative of the amount of UVB radiation received.

Consequently, the compositions containing these photoprotective polymers provide a safer method to take sunbaths than conventional sunscreen products, since protection increases with time of sun exposure and dose of radiation.

Therefore, in another aspect the present invention relates to the use of a photoprotective polymer as defined above in the preparation of a cosmetic or dermatological composition for protecting a human or animal living body from UV radiation.

In another aspect the present invention relates to the use of a photoprotective polymer as defined above as photochemical precursors of UV absorbers.

In another aspect, the present invention refers to the use of a photoprotective polymer as defined above in the preparation of a cosmetic or dermatological composition to be applied to human or animal living body, characterized by a progressive UV protection depending on the time to sun exposition and the degree of sun radiation.

In another aspect, the present invention refers to a photoprotective polymer as defined above for it use in protecting a human or animal living body from UV radiation.

Another aspect of the invention refers to a cosmetic or dermatological composition comprising an organosilicon progressive photoprotective polymer as defined above or a mixture thereof.

The present invention also relates to a cosmetic or dermatological composition as mentioned before comprising an effective amount of a polymer as defined above, or a mixture thereof, susceptible to be photochemically converted in situ to a sunscreen compound with enhanced UV protection ability.

In a particular embodiment of the invention, the content of the photoprotective polymers in the cosmetic or dermatological composition ranges from 0.01% and 40% by weight, based on the total weight of the composition. Preferably, the amount falls within the range of 0.05 to 25% by weight, more preferably falls within 0.1 and 15% by weight.

The cosmetic or dermatologic composition of the invention may also contain at least one additional organic sunscreen compound for filtering UVB or UVA rays. In a preferred embodiment, said additional sunscreen compound is selected from avobenzone, 2-ethylhexyl-p-methoxycinnamate, oxybenzone, octyldimethyl p-aminobenzoic acid, dioxybenzone, ethyl-4-[bis(hydroxypropyl)]aminobenzoate, 2-ethylhexyl-2-cyan-3,3-diphenylacrylate, 2-ethylhexylsalicylate, glyceryl p-aminobenzoate, 3,3,5-trimethylcyclohexylsalicylate, methylanthranylate, p-dimethylaminobenzoic acid, 2-ethylhexyl p-dimethylaminobenzoate, 2-phenylbenzimidazole-5-sulfonic acid, 2-p-dimethylaminophenyl-5-sulfoniumbenzoxazoic acid, sulisobenzone, hexyl 2-(4-diethylamino-2-hydroxybenzoyl)benzoate, 2-(4-methylbenzyliden)-camphor, and 4-isopropyldibenzoylmethane.

Furthermore, the composition of the invention may additionally contain usual adjuvants and additives such as preservatives, antioxidants, fatty substances, oil, water, organic solvents, silicones, thickeners, softeners, emulsifiers, antifoaming agents, moisturizers, fragrances, surfactants, fillers, sequestering agents, anionic, cationic, nonionic or amphoteric polymers or mixtures thereof, propellants acidifying or basifying agents, dyes, colorants, pigments, nanopigments, or any other ingredient usually formulated into cosmetics, in particular those for the production of sunscreen compositions.

The necessary amounts of the cosmetic and dermatological adjuvants and additives can, based on the desired product, easily be chosen by a skilled artisan in this field and will be illustrated in the examples, without being limited hereto. In a preferred embodiment of the invention, the content of the adjuvants and/or additives in the cosmetic or dermatological composition ranges from 0.01% and 40% by weight, based on the total weight of the composition. Preferably, this amount falls within the range of 0.05 to 25% by weight, more preferably falls within 0.1 and 15% by weight.

In another particular embodiment, the cosmetic or dermatological composition of the invention comprises a polymer according to the second aspect of the invention or a mixture thereof, characterized in that the content of polymers ranges from 0.01% to 40% by weight, based on the total weight of the composition, preferably from 0.05% to 25%, and more preferably from 0.01% to 15%, and a sunscreen compound, which is selected from avobenzone, 2-ethylhexyl-p-methoxycinnamate, oxybenzone, octyldimethyl p-aminobenzoic acid, dioxybenzone, ethyl-4-[bis(hydroxypropyl)]aminobenzoate, 2-ethylhexyl-2-cyan-3,3-diphenylacrilate, 2-ethylhexylsalicilate, glyceryl p-aminobenzoate, 3,3,5-trimethylcyclohexylsalicylate, methylanthranilate, p-dimethylaminobenzoic acid, 2-ethylhexyl p-dimethylaminobenzoate, 2-phenylbenzimidazole-5-sulfonic acid, 2-p-dimethylaminophenyl-5-sulfoniumbenzoxazoic acid, sulisobenzone, hexyl 2-(4-diethylamino-2-hydroxybenzoyl)benzoate, 2-(4-methylbenzyliden)-camphor, and 4-isopropyldibenzoylmethane, the content of sunscreen compound ranging from 0.01% to 40% by weight, based on the total weight of the composition, preferably from 0.05% to 25%, and more preferably from 0.01% to 15% to be applied to human or animal living body.

The cosmetic or dermatological composition of the invention can, in particular, be provided in the form of creams, ointments, milks, suspensions, powders, oils, lotions, gels, sticks, foams, emulsions, dispersions, sprays, aerosols, lipsticks, foundations, make-up, loose or press powders, eye blushes, eye shadows, mascaras, nail varnishes, nail lacquers, and non permanent dyeing compositions for the hair.

In another aspect, the present invention refers to a monomer of formula (I) according to the eighth aspect of the invention.

In a preferred embodiment, the present invention refers to a monomer of formula (I) wherein $R_1$, $R_2$, $R_3$, $R_4$ and $R_5$ are H and p is 3.

In another preferred embodiment, the present invention refers to a monomer of formula (I) wherein R is (i) or (ii); Ra is a linear ($C_1$-$C_6$)alkyl; Rb is a linear ($C_1$-$C_6$)alkyl; and Rc is a linear ($C_1$-$C_6$)alkyl. Even more preferably, R is (i) or (ii); $R_1$, $R_2$, $R_3$, $R_4$ and $R_5$ are H; p is 3; Ra is a linear ($C_1$-$C_6$)alkyl; Rb is a linear ($C_1$-$C_6$)alkyl; and Rc is a linear ($C_1$-$C_6$)alkyl.

In another preferred embodiment, the present invention refers to a monomer of formula (I) wherein R is (iii) or (iv), Ra is a linear ($C_1$-$C_6$)alkyl, Rb is a linear ($C_1$-$C_6$)alkyl, and Rc is a linear ($C_1$-$C_6$)alkyl. Even more preferably, R is (iii) or (iv); $R_1$, $R_2$, $R_3$, $R_4$ and $R_5$ are H; p is 3; Ra is a linear ($C_1$-$C_6$)alkyl; Rb is a linear ($C_1$-$C_6$)alkyl; and Rc is a linear ($C_1$-$C_6$)alkyl.

In another preferred embodiment, the monomer of formula (I) is selected from the group consisting of:
3-(3-(triethoxysilyl)propylcarbamoyloxy)phenyl benzoate;
3-(3-(triethoxysilyl)propylamino)phenyl benzoate;
3-(bis(3-(triethoxysilyl)propyl)amino)phenyl benzoate;
3-(3-(3-(triethoxysilyl)propyl)ureido)phenyl benzoate;
4-((3-(triethoxysilyl)propoxy)methyl)phenyl benzoate;
4-((3-(triethoxysilyl)propylcarbamoyloxy)methyl)phenyl benzoate;
4-(3-(triethoxysilyl)propoxy)phenyl benzoate;
4-(3-(triethoxysilyl)propylcarbamoyloxy)phenyl benzoate;
4-(3-(triethoxysilyl)propylamino)phenyl benzoate;
4-(bis(3-(triethoxysilyl)propyl)amino)phenyl benzoate; and
4-(3-(3-(triethoxysilyl)propyl)ureido)phenyl benzoate.

In another aspect, the present invention refers to a process for the preparation of a monomer of formula (I) as defined above when R is a group (i) or (ii), which comprises the reaction of a compound of formula (II') with a compound of formula (III') according to the ninth aspect of the invention.

The present invention also relates to a process for the preparation of a monomer of formula (I) as defined above, when R is a group (iii) or (iv), which comprises the reaction of a compound of formula (II'') with a compound of formula (III'') according to the tenth aspect of the invention.

Compounds of formula (II'), (III'), (II'') and (III'') are prepared from commercially available starting reactants by conventional known methods of organic chemistry as described in the examples provided in the present specification.

Cosmetically or dermatologically acceptable salts of the monomers of formula (I) are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred.

The following examples are provided to further illustrate certain embodiments of the invention and cannot be considered as restricting the scope of the invention in any way.

EXAMPLES

As used herein, the term "Active ingredient" and "Active Ingredient 1" refer to any polymer compound disclosed in examples 12-23.

As used herein, the terms "Active Ingredient 2" and "Active Ingredient 3" refer to any commonly accepted sunscreen compound. Non-limitative examples of such compounds are avobenzone, 2-ethylhexyl-p-methoxycinnamate, oxybenzone, octyldimethyl p-aminobenzoic acid, dioxybenzone, ethyl-4-[bis(hydroxypropyl)]aminobenzoate, 2-ethylhexyl-2-cyan-3,3-diphenylacrylate, 2-ethylhexylsalicylate, glyceryl p-aminobenzoate, 3,3,5-trimethylcyclohexylsalicylate, methylanthranylate, p-dimethylaminobenzoic acid, 2-ethylhexyl p-dimethylaminobenzoate, 2-phenylbenzimidazole-5-sulfonic acid, 2-p-dimethylaminophenyl-5-sulfoniumbenzoxazoic acid, sulisobenzone, hexyl 2-(4-diethylamino-2-hydroxybenzoyl)benzoate, 2-(4-methylbenzyliden)-camphor, and 4-isopropyldibenzoylmethane and the like.

Example 1

3-(3-(Triethoxysilyl)propylcarbamoyloxy)phenyl benzoate

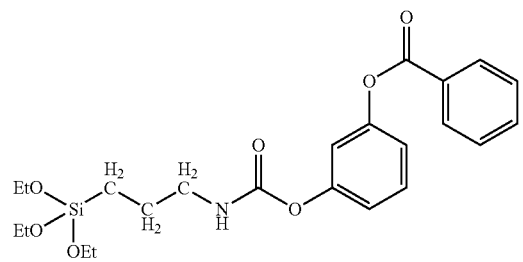 [SMILES: CCO[Si](CCCNC(=O)Oc1cccc(OC(=O)c2ccccc2)c1)(OCC)OCC]

Resorcinol monobenzoate (866 mg, 4.043 mmol), triethylamine (0.56 mL, 4.043 mmol) and triethoxy (3-isocianatepropyl)silane (1 mL, 4.043 mmol) were dissolved in 25 mL of chloroform. The solution was refluxed for 12 hours, cooled and the solvent was removed under reduced pressure. The obtained crude was washed with pentane, thus affording 1.864 g (4.041 mmol, yield=99%) of a yellowish oil corresponding to the compound of the title (HPLC purity=99%).

$^1$H-NMR (CDCl$_3$, 400 MHz): 8.19 ppm (dd, 2H$_{Ar}$), 7.63 ppm (td, 1H$_{Ar}$), 7.50 ppm (t, 2H$_{Ar}$), 7.25 ppm (t, 1H$_{Ar}$), 6.75 ppm (m, 3H$_{Ar}$), 5.81 ppm (s, 1H, NH), 3.84 ppm (q, 3×2H, O—CH$_2$—CH$_3$), 3.29 ppm (t, 2H, HN—CH$_2$—CH$_2$), 1.73 ppm (q$_u$, 2H, CH$_2$), 1.22 ppm (t, 3×3H, O—CH$_2$—CH$_3$), 0.67 ppm (q$_u$, 2H, Si—CH$_2$)

$^{13}$C-NMR (CDCl$_3$, 400 MHz): 165.32, 156.82, 151.76, 133.66, 130.18, 130.09, 129.40, 128.57, 113.66, 113.21, 109.35, 70.08, 58.50, 45.36, 25.07, 18.24, 7.53

IR (melted film): 3454.20, 2974.41, 2270.78, 1712.94, 1507.50, 1081.26

Example 2

3-(3-(Triethoxysilyl)propylamino)phenyl benzoate and

Example 3

3-(Bis(3-(triethoxysilyl)propyl)amino)phenyl benzoate

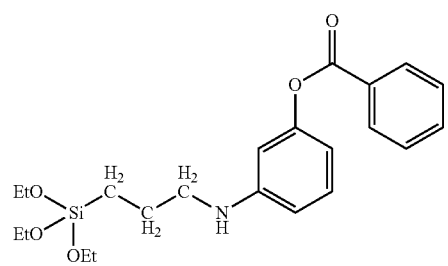

-continued

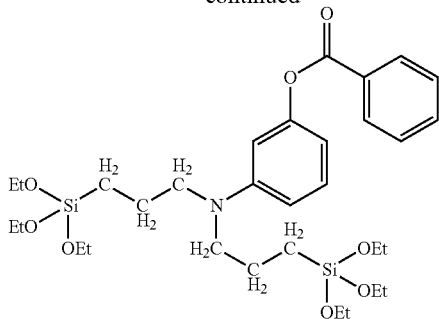

a) 3-Nitrophenyl benzoate preparation

3-Nitrophenol (1.716 g, 12.346 mmol) and triethylamine (1.6 mL, 12.346 mmol) were dissolved in 50 mL of dichloromethane. The solution was shaken 30 minutes at room temperature. Benzoyl chloride (1.43 mL, 12.346 mmol) was added drop by drop and the resulting solution was shaken at room temperature until full conversion as determined by thin-layer chromatography. Carbonated water (20 mL) was added three times. The organic phase was dried over magnesium sulfate, filtered and the solvent was removed under reduced pressure, thus affording 2.7080 g of a white solid corresponding to 3-nitrophenyl benzoate (11.144 mmol, yield=90%).

$^1$H-NMR (CDCl$_3$, 400 MHz): 8.21 ppm (dd, 2H$_{Ar}$), 8.16 ppm (m, 2H$_{Ar}$), 7.68 ppm (tt, 1H$_{Ar}$), 7.61 ppm (m, 2H$_{Ar}$), 7.53 ppm (t, 2H$_{Ar}$)

b) 3-Aminophenyl benzoate preparation

3-Nitrophenyl benzoate (2.7080 g, 11.144 mmol) and tin (II) chloride dihydrate (12.564 g, 55.720 mmol) were dissolved in 60 mL of ethanol and heated at 100° C. for 1 hour. The reaction crude was allowed to cool to room temperature, and an aqueous solution of sodium carbonate was added until pH 8. The crude material was extracted with dichloromethane (3×50 mL), magnesium sulfate was added to the organic phase, filtered and the solvent was removed under reduced pressure, thus affording 2.374 g (11.143 mmol, yield=100%) of 3-aminophenyl benzoate.

$^1$H-NMR (CDCl$_3$, 400 MHz): 8.19 ppm (dd, 2H$_{Ar}$), 7.63 ppm (td, 1H$_{Ar}$), 7.50 ppm (t, 2H$_{Ar}$), 7.18 ppm (t, 1H$_{Ar}$), 6.59 ppm (m, 3H$_{Ar}$), 3.45 ppm (sa, 2H, NH$_2$)

$^{13}$C-NMR (CDCl$_3$, 400 MHz): 165.15, 151.95, 147.56, 133.47, 130.12, 139.69, 128.51, 112.75, 111.59, 108.48 c) 3-(3-(Triethoxysilyl)propylamino)phenyl benzoate and 3-(bis(3-(Triethoxysilyl)propyl)amino)phenyl benzoate preparation 3-Aminophenyl benzoate (504 mg, 2.334 mmol), potassium carbonate (645 mg (4.668 mmol), potassium iodide (1.550 g, 9.336 mmol), and (3-chloropropyl)triethoxysilane (2 mL, 9.334 mmol) were dissolved in 25 mL of acetonitrile. The resultant solution was refluxed for 36 hours, allowed to cool, filtered, and the solvent was removed under reduced pressure. The crude was purified by flash chromatography (hexane/ethyl acetate 8:2) to afford 456 mg (1.093 mmol, yield=47%) of mono-silyl compound (HPLC purity=90%) and 235 mg (0.378 mmol, yield=16%) of di-silyl compound (HPLC purity=97%).

Mono-silyl compound:
$^1$H-NMR (CDCl$_3$, 400 MHz): 8.19 ppm (dd, 2H$_{Ar}$), 7.63 ppm (td, 1H$_{Ar}$), 7.50 ppm (t, 2H$_{Ar}$), 7.18 ppm (t, 1H$_{Ar}$), 6.50 ppm (tt, 2H$_{Ar}$), 6.43 ppm (t, 1H$_{Ar}$), 3.83 ppm (q, 3×2H, O—CH$_2$—CH$_3$), 3.13 ppm (t, 2H, HN—CH$_2$—CH$_2$), 1.74 ppm (q$_u$, 2H, CH$_2$), 1.23 ppm (t, 3×3H, O—CH$_2$—CH$_3$), 0.70 ppm (q$_u$, 2H, Si—CH$_2$)

$^{13}$C-NMR (CDCl$_3$, 400 MHz): 165.19, 152.29, 149.32, 133.27, 130.09, 129.98, 129.73, 128.41, 109.08, 108.00, 104.55, 60.36, 58.40, 31.57, 20.28, 14.09, 7.48

IR (film CH$_2$Cl$_2$): 3402.20, 2974.08, 1736.64, 1615.95, 1265.96, 1152.48, 1081.02

Di-silyl compound:
$^1$H-NMR (CDCl$_3$, 400 MHz): 8.19 ppm (dd, 2H$_{Ar}$), 7.63 ppm (td, 1H$_{Ar}$), 7.50 ppm (t, 2H$_{Ar}$), 7.18 ppm (t, 1H$_{Ar}$), 6.50 ppm (tt, 2H$_{Ar}$), 6.43 ppm (t, 1H$_{Ar}$), 3.83 ppm (q, 6×2H, O—CH$_2$—CH$_3$), 3.13 ppm (t, 2×2H, N—CH$_2$—CH$_2$), 1.74 ppm (q$_u$, 2×2H, CH$_2$), 1.23 ppm (t, 6×3H, O—CH$_2$—CH$_3$), 0.70 ppm (q$_u$, 2×2H, Si—CH$_2$)

$^{13}$C-NMR (CDCl$_3$, 400 MHz): 165.19, 152.16, 149.70, 133.34, 130.10, 129.87, 129.84, 128.46, 110.41, 109.79, 105.52, 60.36, 58.43, 31.57, 21.01, 14.09, 7.79

IR (film CH$_2$Cl$_2$): 2974.11, 1737.22, 1514.41, 1003.23, 1081.16

Example 4

3-(3-(3-(Triethoxysilyl)propyl)ureido)phenyl benzoate

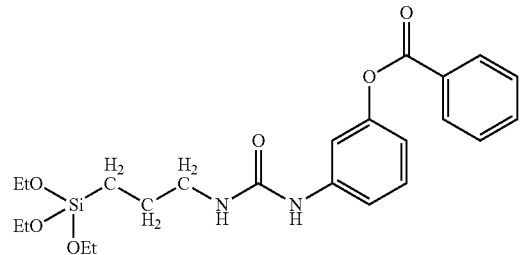 [SMILES: CCO[Si](CCCNC(=O)Nc1cccc(OC(=O)c2ccccc2)c1)(OCC)OCC]

3-Aminophenyl benzoate (862 mg, 4.043 mmol) (prepared according to Example 2a) b)), triethylamine (0.56 mL, 4.043 mmol), and triethoxy (3-isocianatepropyl)silane (1 mL, 4.043 mmol) were dissolved in 25 mL of chloroform. The resultant solution was refluxed for 12 hours, allowed to cool, and the solvent was removed under reduced pressure. The obtained crude was washed with pentane, filtered, and washed again with 10 mL of pentane, thus affording 1.334 g (2.899 mmol, yield=72%) of a yellowish solid corresponding to the compound of the title (HPLC purity>99.7%).

$^1$H-NMR (CDCl$_3$, 400 MHz): 8.19 ppm (dd, 2H$_{Ar}$), 7.64 ppm (td, 1H$_{Ar}$), 7.52 ppm (t, 2H$_{Ar}$), 7.38 ppm (t, 1H, NH), 7.23 ppm (t, 1H$_{Ar}$), 7.09 ppm (dd, 2H$_{Ar}$), 6.82 ppm (dd, 1H$_{Ar}$), 5.27 ppm (t, 1H, NH), 3.80 ppm (q, 3×2H, O—CH$_2$—CH$_3$), 3.17 ppm (t, 2H, HN—CH$_2$—CH$_2$), 1.58 ppm (q$_u$, 2H, CH$_2$), 1.19 ppm (t, 3×3H, O—CH$_2$—CH$_3$), 0.61 ppm (q$_u$, 2H, Si—CH$_2$)

$^{13}$C-NMR (CDCl$_3$, 400 MHz): 165.49, 155.47, 151.33, 140.52, 140.42, 133.64, 130.16, 129.37, 128.53, 117.12, 115.81, 113.24, 58.44, 46.02, 42.64, 23.48, 18.27, 8.54, 7.61

IR (KBr): 3322.14, 2974.93, 1733.06, 1646.51, 1259.31, 1081.35

Example 5

4-((3-(Triethoxysilyl)propoxy)methyl)phenyl benzoate

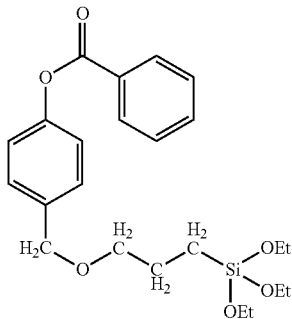 [SMILES: CCO[Si](CCCOCc1ccc(OC(=O)c2ccccc2)cc1)(OCC)OCC]

a) 4-Formilphenyl benzoate preparation

4-Hydroxybenzaldehide (1.080, g 8.85 mmol), and triethylamine (1.5 mL, 10.78 mmol) were dissolved in 25 mL of dichloromethane. The solution was shaken 30 minutes at room temperature. Benzoyl chloride (1 mL, 8.85 mmol) was added drop by drop and the resulting solution was shaken at room temperature for 1 hour. A saturated aqueous solution of sodium carbonate (20 mL) was added three times. The organic phase was dried over magnesium sulfate, filtered and the solvent was removed under reduced pressure, thus affording 1.8821 g (8.324 mmol, yield=94%) of 4-formilphenyl benzoate.

$^1$H-NMR (CDCl$_3$, 400 MHz): 10.06 ppm (s, 1H, CHO), 8.20 ppm (dd, 2H$_{Ar}$), 7.99 ppm (td, 2H$_{Ar}$), 7.67 ppm (tt, 1H$_{Ar}$), 7.55 ppm (tt, 2H$_{Ar}$), 7.42 ppm (td, 2H$_{Ar}$)

$^{13}$C-NMR (CDCl$_3$, 400 MHz): 190.90, 164.47, 155.67, 134.06, 134.00, 131.25, 130.26, 128.90, 128.70, 122.52, 109.99 b) 4-(Hydroxymethyl)phenyl benzoate preparation b.1) 4-(Hydroxymethyll)phenol (1.087 g, 8.77 mmol) and triethylamine (1.3 mL, 8.77 mmol) were dissolved in 25 mL of dichloromethane. The solution was shaken at 0° C. for 30 minutes. Benzoyl chloride (1 mL, 8.77 mmol) was added drop by drop and the resulting solution was shaken at 0° C. for 5 hours. Saturated aqueous solution of sodium carbonate (20 mL) was added three times. The organic phase was dried over magnesium sulfate, filtered, and the solvent was removed under reduced pressure, thus affording a yellowish solid that upon recrystallization from cyclohexane provided 1.600 g (70.16 mmol, yield=80%) of 4-(hydroxymethyl)phenyl benzoate.

$^1$H-NMR (CDCl$_3$, 400 MHz): 8.21 ppm (dd, 2H$_{Ar}$), 7.65 ppm (tt, 1H$_{Ar}$), 7.52 ppm (t, 2H$_{Ar}$), 7.42 ppm (d, 2H$_{Ar}$), 7.19 ppm (d, 2H$_{Ar}$), 4.69 ppm (s, 2H, CH$_2$OH)

$^{13}$C-NMR (CDCl$_3$, 400 MHz): 165.24, 150.33, 138.55, 133.61, 133.09, 130.18, 130.16, 129.69, 129.50, 129.45, 128.56, 128.39, 128.12, 121.90, 64.77 b.2) 4-Formilphenyl benzoate (1.8821 g, 8.234 mmol) was dissolved in 50 mL of ethanol and the resultant solution shaken in an ice bath. Sodium borohydride (1 g, 26.55 mmol) was added portionwise over a period of 10 minutes. The reaction was controlled by thin-layer chromatography. Upon the reaction was completed, 20 mL of water were added and the mixture shaken at 0° C. for 10 minutes. The product was extracted with chloroform (3×50 mL), the organic phase was dried over magnesium sulfate, filtered, and the solvent was removed under reduced pressure, thus affording 1.890 g (8.289 mmol, yield=100%) of 4-formilphenyl benzoate.

$^1$H-NMR (CDCl$_3$, 400 MHz): 8.21 ppm (dd, 2H$_{Ar}$), 7.65 ppm (tt, 1H$_{Ar}$), 7.52 ppm (t, 2H$_{Ar}$), 7.42 ppm (d, 2H$_{Ar}$), 7.19 ppm (d, 2H$_{Ar}$), 4.69 ppm (s, 2H, CH$_2$OH)

$^{13}$C-NMR (CDCl$_3$, 400 MHz): 165.24, 150.33, 138.55, 133.61, 133.09, 130.18, 130.16, 129.69, 129.50, 129.45, 128.56, 128.39, 128.12, 121.90, 64.77 c) (3-Iodopropyl)triethoxysilane preparation

Sodium iodide (15 g, 93.325 mmol) was dissolved in acetone and (3-chloropropyl)triethoxysilane (22 mL, 45.63 mmol) was added dropwise. The resultant mixture was shaken at 80° C. for 48 hours in argon. The reaction crude was cooled to room temperature, filtered and the solvent was removed under reduced pressure. A yellowish liquid (28.476 g) containing 90% of iodinated compound and 10% of the chlorinated reagent was obtained. Said liquid was kept for further use without purification.

$^1$H-NMR (CDCl$_3$, 400 MHz): 3.80 ppm (q, 3×2H, O—CH$_2$—CH$_3$), 3.20 ppm (t, 2H, I—CH$_2$ CH$_2$), 1.87 ppm (q$_u$, 2H, CH$_2$), 1.20 ppm (t, 3×3H, O—CH$_2$—CH$_3$), 0.71 ppm (q$_u$, 2H, Si—CH$_2$)

$^{13}$C-NMR (CDCl$_3$, 400 MHz): 58.42, 27.53, 18.25, 12.22, 10.65 d) 4-((3-(Triethoxysilyl)propoxy)methyl)phenyl benzoate preparation 4-(Hydroxymethyl)phenyl benzoate (1 g, 4.39 mmol) was dissolved in 20 mL of anhydrous tetrahydrofuran and cooled in an ice bath. A suspension of sodium hydride (60% suspension, 175 mg, 4.39 mmol) in 5 mL of anhydrous tetrahydrofuran was added dropwise under stirring. The resultant mixture was stirred at 0° C. for 1 hour. (3-Iodopropyl)triethoxysilane (1.46 g, 4.39 mmol) was added and the mixture was refluxed for 36 hours. The reaction crude was filtered, the solvent was removed under reduced pressure, and the resultant oil was chromatographed (hexane/ethyl acetate 8:2) thus affording 570 mg (1.32 mmol, yield=30%) of the title compound (HPLC purity=99.2%).

$^1$H-NMR (CDCl$_3$, 400 MHz): 8.21 ppm (dd, 2H$_{Ar}$), 7.66 ppm (tt, 1H$_{Ar}$), 7.50 ppm (tt, 2H$_{Ar}$), 7.45 ppm (d, 2H$_{Ar}$), 7.20 ppm (d, 2H$_{Ar}$), 4.73 ppm (s, 2H, —CH$_2$—O), 3.80 ppm (q, 3×2H, O—CH$_2$—CH$_3$), 3.19 ppm (t, 2H, O—CH$_2$—CH$_2$), 1.90 ppm (q$_u$, 2H, CH$_2$), 1.20 ppm (t, 3H, O—CH$_2$—CH$_3$), 0.70 ppm (q$_u$, 2H, Si—CH$_2$)

$^{13}$C-NMR (CDCl$_3$, 400 MHz): 165.24, 150.36, 138.51, 133.60, 130.18, 130.16, 129.50, 129.45, 128.56, 128.12, 121.82, 64.83, 58.42, 27.53, 26.87, 18.25, 12.22, 10.65

Example 6

4-((3-(Triethoxysilyl)propylcarbamoyloxy)methyl) phenyl benzoate

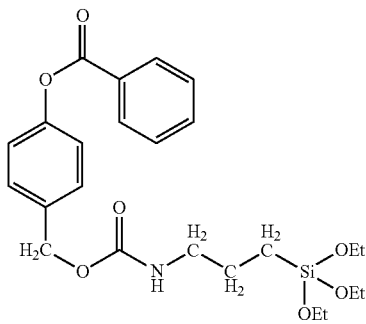 [SMILES: CCO[Si](CCCNC(=O)OCc1ccc(OC(=O)c2ccccc2)cc1)(OCC)OCC]

4-(Hydroxymethyl)phenyl benzoate (Example 5 a) b.1)), (0.25 mL, 1.785 mmol), triethylamine (407 mg, 1.785 mmol), and triethoxy(3-isocianatepropyl)silane (0.44 mL, 1.785 mmol) were dissolved in 25 mL of chloroform. The resultant solution was refluxed and the reaction was controlled by thin-layer chromatography. The solvent was removed under reduced pressure, 30 mL of hexane/ethyl acetate 2:1 were added, the formed solid was filtrated, and the solvent was removed under reduced pressure, thus affording an oil (726 mg, 1.528 mmol, yield=86%) corresponding to title compound (HPLC purity=97%).

$^1$H-NMR (CDCl$_3$, 400 MHz): 8.20 ppm (dd, 2H$_{Ar}$), 7.66 ppm (tt, 1H$_{Ar}$), 7.51 ppm (tt, 2H$_{Ar}$), 7.43 ppm (d, 2H$_{Ar}$), 7.20 ppm (d, 2H$_{Ar}$), 5.11 ppm (s, 2H, —CH$_2$—O), 3.83 ppm (q, 3×2H, O—CH$_2$—CH$_3$), 3.23 ppm (t, 2H, NH—CH$_2$—CH$_2$), 1.66 ppm (q$_u$, 2H, CH$_2$), 1.22 ppm (t, 3H, O—CH$_2$—CH$_3$), 0.66 ppm (q$_u$, 2H, Si—CH$_2$)

$^{13}$C-NMR (CDCl$_3$, 400 MHz): 165.07, 156.27, 150.65, 134.43, 133.60, 129.45, 128.55, 121.73, 65.84, 58.44, 43.45, 25.10, 23.25, 18.26, 7.62, 7.54

IR (film): 3343.96, 2974.20, 2271.66, 1729.38, 1510.85, 1264.81, 1079.31

Example 7

4-(3-(Triethoxysilyl)propoxy)phenyl benzoate

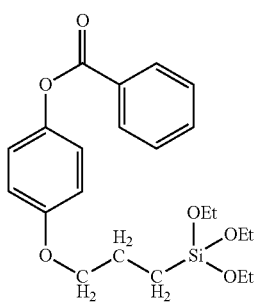 [SMILES: CCO[Si](CCCOc1ccc(OC(=O)c2ccccc2)cc1)(OCC)OCC]

4-Hydroxyphenyl benzoate (0.5 g, 2.334 mmol), potassium carbonate (0.323 g, 2.334 mmol), and potassium iodide (0.775 g, 4.667 mmol) were dissolved in acetonitrile. The resultant solution was refluxed for 36 hours, filtered, the solvent evaporated under reduced pressure, and the obtained crude was purified by flash chromatography by using hexane/ethyl acetate 8:2 as eluent, thus affording 488 mg (1.167 mmol, yield=50%) of the title compound (HPLC purity=99%).

$^1$H-NMR (CDCl$_3$, 400 MHz): 8.22 ppm (dd, 2H$_{Ar}$), 7.70 ppm (t, 1H$_{Ar}$), 7.60 ppm (t, 2H$_{Ar}$) 7.20 ppm (dd, 2H$_{Ar}$), 7.05 ppm (dd, 2H$_{Ar}$), 4.06 ppm (t, 2H, O—CH$_2$), 3.84 ppm (q, 3×2H, O—CH$_2$—CH$_3$), 1.70 ppm (q$_u$, 2H, CH$_2$), 1.20 ppm (t, 3×3H, O—CH$_2$—CH$_3$), 0.70 ppm (q$_u$, 2H, Si—CH$_2$)

$^{13}$C-NMR (CDCl$_3$, 400 MHz): 165.2, 156.2, 151.76, 133.60, 130.28, 130.19, 129.44 128.59, 113.64, 113.17, 109.30, 70.00, 58.56, 45.34, 25.05, 18.23, 7.50

IR (KBr): 2974.5, 1739.6, 1610.8, 1591.8, 1489.5, 1472.2, 1452.0, 1081.5, 777.5

Example 8

4-(3-(Triethoxysilyl)propylcarbamoyloxy)phenyl benzoate

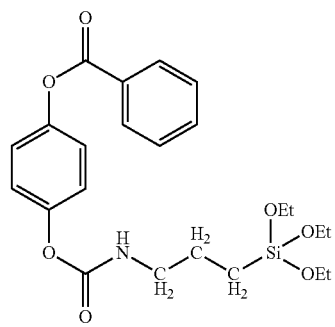 [SMILES: CCO[Si](CCCNC(=O)Oc1ccc(OC(=O)c2ccccc2)cc1)(OCC)OCC]

4-Hydroxyphenyl benzoate (433 mg, 2.022 mmol), triethylamine (0.28 mL, 2.022 mmol), and triethoxy(3-isocianatepropyl)silane (0.5 mL, 2.022 mmol) were dissolved in 25 mL of chloroform. The resultant solution was refluxed for 12 hours, cooled at room temperature, and the solvent removed at reduced pressure. Cool pentane was added, the formed precipitate was filtered, and washed with 10 mL of additional pentane, thus affording 930 mg (1.961 mmol, yield=97%) of the title compound (HPLC purity=99%).

$^1$H-NMR (CDCl$_3$, 400 MHz): 8.20 ppm (dd, 2H$_{Ar}$), 7.63 ppm (t, 1H$_{Ar}$), 7.51 ppm (t, 2H$_{Ar}$) 7.07 ppm (dd, 2H$_{Ar}$), 6.85 ppm (dd, 2H$_{Ar}$), 5.28 ppm (sa, 1H, NH), 3.82 ppm (q, 3×2H, O—CH$_2$CH$_3$), 3.21 ppm (t, 2H, NH—CH$_2$), 1.73 ppm (q$_u$, 2H, CH$_2$), 1.22 ppm (t, 3×3H, O—CH$_2$—CH$_3$), 0.68 ppm (q$_u$, 2H, Si—CH$_2$)

$^{13}$C-NMR (CDCl$_3$, 400 MHz): 165.32, 153.30, 133.53, 128.53, 122.57, 116.04, 58.48, 45.37, 25.09, 18.26, 7.54

IR (KBr): 3452.59, 3348.26, 2974.41, 2271.41, 1712.67, 1508.18, 1079.92

Example 9

4-(3-(Triethoxysilyl)propylamino)phenyl benzoate and

Example 10

4-(Bis(3-(triethoxysilyl)propyl)amino)phenyl benzoate

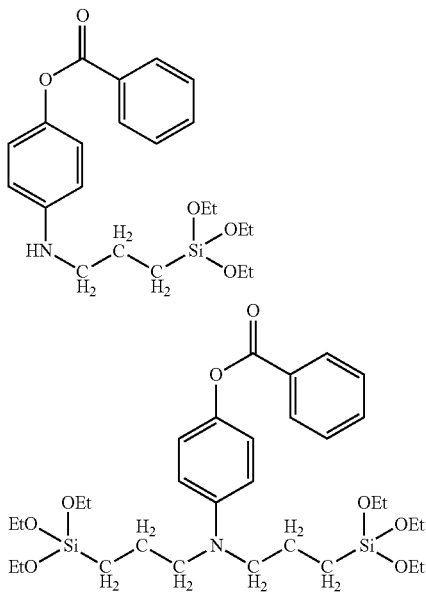

3-Aminophenyl benzoate (504 mg, 2.334 mmol) (prepared according to Example 2 a) b)), potassium carbonate (645 mg, 4.668 mmol), potassium iodide (1.550 g, 9.336 mmol), and 3-chloropropyl)triethoxysilane (2 mL, 9.334 mmol) were dissolved in 25 mL of acetonitrile. The resultant solution was refluxed for 36 hours, allowed to cool, filtrated, and the solvent was evaporated under reduced pressure. The crude was purified by flash chromatography (hexane/ethyl acetate 8:2) to give 438 mg (1.050 mmol, yield=45%) of mono-silyl compound (HPLC purity=83%) and 218 mg (0.350 mmol, yield=15%) of di-silyl compound (HPLC purity=88%).

Mono-silyl compound:
$^1$H-NMR (CDCl$_3$, 400 MHz): 8.20 ppm (dd, 2H$_{Ar}$), 7.60 ppm (td, 1H$_{Ar}$), 7.49 ppm (t, 2H$_{Ar}$) 7.02 ppm (dd, 2H$_{Ar}$), 6.67 ppm (dd, 2H$_{Ar}$), 3.80 ppm (q, 3×2H, O—CH$_2$—CH$_3$), 3.25 ppm (t, 2H, HN—CH$_2$—CH$_2$), 1.71 ppm (q$_u$, 2H, CH$_2$), 1.22 ppm (t, 3×3H, O—CH$_2$—CH$_3$), 0.62 ppm (q$_u$, 2H, Si—CH$_2$)

$^{13}$C-NMR (CDCl$_3$, 400 MHz): 165.77, 146.37, 141.92, 133.26, 128.44, 122.11, 112.99, 58.44, 46.74, 30.90, 22.74, 18.30, 7.82, 7.53

IR (film CH$_2$Cl$_2$): 3399.65, 2973.99, 1733.37, 1610.76, 1515.34, 1268.00, 1198.14, 1082.04

Di-silyl Compound:
$^1$H-NMR (CDCl$_3$, 400 MHz): 8.20 ppm (dd, 2H$_{Ar}$), 7.60 ppm (td, 1H$_{Ar}$), 7.49 ppm (t, 2H$_{Ar}$) 7.02 ppm (dd, 2H$_{Ar}$), 6.67 ppm (dd, 2H$_{Ar}$), 3.80 ppm (q, 6×2H, O—CH$_2$—CH$_3$), 3.25 ppm (t, 2×2H, N—CH$_2$—CH$_2$), 1.71 ppm (q$_u$, 2×2H, CH$_2$), 1.22 ppm (t, 6×3H, O—CH$_2$—CH$_3$), 0.62 ppm (q$_u$, 2×2H, Si—CH$_2$)

$^{13}$C-NMR (CDCl$_3$, 400 MHz): 165.85, 146.10, 140.56, 133.19, 130.05, 128.41, 121.93, 111.89, 58.40, 53.84, 47.47, 30.89, 26.48, 20.33, 18.41, 18.30, 8.04, 7.53, 7.05

IR (film CH$_2$Cl$_2$): 2974.02, 1738.21, 1612.95, 1500.92, 1264.55, 1081.06

Example 11

4-(3-(3-(Triethoxysilyl)propyl)ureido)phenyl benzoate

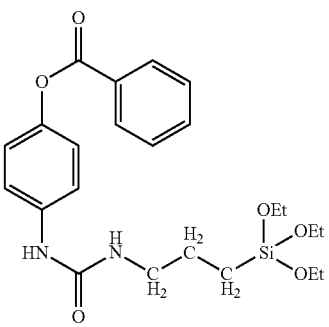 [SMILES: CCO[Si](CCCNC(=O)Nc1ccc(OC(=O)c2ccccc2)cc1)(OCC)OCC]

3-Aminophenyl benzoate (461 mg, 2.162 mmol) (prepared according to Example 2 a) b)), triethylamine (0.30 mL, 2.162 mmol), and triethoxy(3-isocianatepropyl)silane (0.54 mL, 2.162 mmol) were dissolved in 25 mL of chloroform. The resultant solution was refluxed for 12 hours, cooled to room temperature, and the solvent removed under reduced pressure. Cool pentane was added, the formed precipitate was filtered, and washed with 10 mL of additional pentane, thus affording 945 mg (2.954 mmol, yield=95%) of the title compound (HPLC purity=98%).

$^1$H-NMR (CDCl$_3$, 400 MHz): 8.20 ppm (dd, 2H$_{Ar}$), 7.64 ppm (t, 1H$_{Ar}$), 7.53 ppm (t, 2H$_{Ar}$) 7.35 ppm (dd, 2H$_{Ar}$), 7.14 ppm (dd, 2H$_{Ar}$), 6.64 ppm (sa, 1H, NH), 5.10 ppm (t, 1H, NH), 3.81 ppm (q, 3×2H, O—CH$_2$CH$_3$), 3.25 ppm (t, 2H, NH—CH$_2$), 1.73 ppm (q$_u$, 2H, CH$_2$), 1.20 ppm (t, 3×3H, O—CH$_2$—CH$_3$), 0.66 ppm (q$_u$, 2H, Si—CH$_2$)

$^{13}$C-NMR (CDCl$_3$, 400 MHz): 165.54, 155.67, 146.58, 136.59, 133.64, 128.57, 122.20, 121.83, 58.47, 42.71, 23.51, 18.28, 7.62

IR (KBr): 3353.45, 3267.08, 2973.52, 1732.54, 1646.99, 1565.24, 1506.69, 1196.01, 1080.61

Example 12

3-(3-(Triethoxysilyl)propoxy)phenyl benzoate particles (P1)

1) Preparation

A mixture of ethanol (3.8 mL, 0.082 mmol) and deionized water (1.4 mL, 0.078 mmol) was heated in a water bath to 60° C. with stirring. A mixture of tetraethoxy silane, (TEOS, 396 mg, 1.903 mmol), and 3-(3-(triethoxysilyl)propoxy)phenyl benzoate (U.S. Pat. No. 4,328,346, 1.328 g, 3.172 mmol) was heated with no stirring in the same bath. When the ethanol/water mixture temperature attained 60° C., 1.7 mL of 30% of ammonia (0.011 mmol) were added and the stirring was augmented to assure a homogenous mixture. When the temperature attained again 60° C., the solution of TEOS and 3-(3-(triethoxysilyl)propoxy)phenyl benzoate was added and stirred for 15 seconds. The resultant suspension was allowed to stay for 2 hours at 60° C. The formed precipitate was filtered, washed with ethanol (3×20 mL) and dried under vacuum.

The solvent was removed under reduced pressure and the remaining was analyzed by 1H-RMN spectroscopy to determinate the polymerisation is quantitative. The resultant particles comprise a 68% in weight of the precursor, expressed as 3-methoxyphenyl benzoate.

2) Particle Characterization

The obtained particles were characterized by Scanning Electron Microscopy (SEM), size distribution, UV-Vis spectroscopy, IR spectroscopy and HPLC chromatography.

2.1) Particle Morphology

The image by SEM shows spherical particles with 500 nm diameter and homogenous aspect.

Size distribution shows that particles are monodisperse with size 570±170 nm.

2.2) UV-Vis Spectroscopy

A suspension of particles 3% (30 mg/mL) in polydimethylsiloxane (PDMS) having a viscosity of 20 cSt was added to a quartz surface covered with adhesive belt (Transpore®) at 2 mg/cm$^2$. Particles show an intense absorption in UVB region with a queue going to UVA when the UV-Vis spectrum was registered with an integrating sphere in diffuse transmittance mode.

2.3) IR Spectroscopy

IR particles spectrum in KBr pellet show 1735 cm$^{-1}$ y 1100 cm$^{-1}$ bands corresponding to C=O tension of aromatic esters from precursor and O—Si—O from matrix, respectively.

2.4) HPLC Chromatography

Particles hermeticity was determined by extraction with solvents at high temperature, the extracts being analyzed by HPLC. Particles (200 mg) and 100 mL of a mixture of methanol and water ((80:20) were refluxed in a Soxhlet for 5 hours. Solvent samples were analyzed by HPLC under the following conditions:

Equipment: HP 1090 Liquid Chromatograph
Column: Reverse Phase Kromasil C18 5 μm 15×0.46
Mobile Phase: acetonitrile/water 80:20
Flow: 1.0 mL/min
Detection: absorption 254 nm Particles chromatogram showed only a solvent dead point time, thus indicating that particles are essentially hermetic.

3) Particles Phototransformation

Particles, alone or suspended in PDMS, were irradiated at 35° C. in a Luzchem ICH-2 photoreactor provided with 16 UVB lamps (irradiance 70 W/m$^2$).

3.1) UV-Vis Spectroscopy

The 3% particles suspension in PDMS was added to a quartz surface covered with adhesive belt (Transpore®) at 2 mg/cm$^2$. The evolution of photoconversion was controlled by measuring the diffuse transmittance of the sample between 280 and 400 nm.

Particles spectrum shows the irradiated particles absorb both in UVB and UVA regions.

3.2) IR Spectroscopy

IR Spectrum was recorded using a KBr pellet. The most significant changes in comparison with non-irradiated particles were the 1735 cm$^{-1}$ band disappearance and the appearance of another one at 1630 cm$^{-1}$, which is a characteristic of aromatic 6-hydroxyketone C=O strength.

3.3) HPLC Chromatography

HPLC chromatography of irradiated microcapsules was performed in the same way as for non-irradiated microcapsules (2.4).

Particles chromatogram showed only a solvent dead point time, thus indicating that particles are essentially hermetic.

Example 13

3-(3-Triethoxysilyl)propylcarbamoyloxy)phenyl benzoate particles (P2)

Example 14

3-(3-Triethoxysilyl)propylamino)phenyl benzoate particles (P3)

Example 15

3-(Bis(3-(triethoxysilyl)propyl)aminophenyl benzoate particles (P4)

Example 16

3-(3-(3-Triethoxysilyl)propyl)ureido)phenyl benzoate particles (P5)

Example 17

4-((3-(Triethoxysilyl)propoxy)methyl)phenyl benzoate particles (P6)

Example 18

4-((3-(Triethoxysilyl)propylcarbamoyloxy)methyl) phenyl benzoate (P7)

Example 19

4-(3-(Triethoxysilyl)propoxy)phenyl benzoate particles (P8)

Example 20

4-(3-(Triethoxysilyl)propylcarbamoyloxy)phenyl benzoate particles (P9)

Example 21

4-(3-(Triethoxysilyl)propylamino)phenyl benzoate particles (P10)

Example 22

4-(Bis(3-(Triethoxysilyl)propylamino)phenyl benzoate particles (P11)

Example 23

4-(3-(3-Triethoxysilyl)propyl)ureido)phenyl benzoate particles (P12)

Compounds of Examples 13-23 were prepared from appropriate reagents following the synthesis described in Example 12. HPLC hermeticity was assessed for all compounds. Preparative and analytical details are summarized in Table 1.

TABLE 1

| Ex. | Reactants mg (mmol) TEOS | Reactants mg (mmol) Monomer | Ammonia 30% mL | Precursor percentage | Particles diameter nm |
|---|---|---|---|---|---|
| 13 | 136 (0.653) | 500 (1.0842) | 1.36 | 60 (1) | 594 ± 36 |
| 14 | 8.2 (0.039) | 69 (0.165) | 0.091 | 81 (2) | 218 ± 8 |
| 15 | 5.5 (0.026) | 69 (0.111) | 0.061 | 62 (3) | 1065 ± 120 |
| 16 | 136 (0.653) | 500 (1.086) | 1.36 | 72 (4) | 510 ± 93 |
| 17 | 136 (0.653) | 469 (1.0842) | 1.36 | 61 (5) | 470 ± 27 |
| 18 | 132 (0.631) | 500 (1.052) | 1.36 | 54 (6) | 833 ± 139 |
| 19 | 7.1 (0.034) | 60 (0.143) | 0.079 | 68 (7) | 1181 ± 129 |
| 20 | 136 (0.653) | 500 (1.0842) | 1.36 | 60 (8) | 116 ± 8 |
| 21 | 13.2 (0.063) | 111 (0.266) | 0.147 | 81 (9) | 1485 ± 154 |
| 22 | 8.5 (0.041) | 107 (0.172) | 0.095 | 62 (10) | 776 ± 56 |
| 23 | 136 (0.653) | 500 (1.0865) | 1.36 | 72 (11) | 154 ± 11 |

(1) expressed as 3-methoxyphenyl benzoate
(2) expressed as 3-(diethylamino)phenyl benzoate
(3) expressed as 3-(diethylamino)phenyl benzoate
(4) expressed as 3-(diethylamino)phenyl benzoate
(5) expressed as 4-methylphenyl benzoate
(6) expressed as 4-methylphenyl benzoate
(7) expressed as 4-methoxyphenyl benzoate
(8) expressed as 4-methoxyphenyl benzoate
(9) expressed as 4-(diethylamino)phenyl benzoate
(10) expressed as 4-(diethylamino)phenyl benzoate
(11) expressed as 4-(diethylamino)phenyl benzoate In the present invention cosmetic or dermatological compositions are selected from creams, ointments, milks, suspensions, powders, oils, lotions, gels, sticks, foams, emulsions, dispersions, sprays, aerosols, lipsticks, foundations, makeup, loose or press powders, eye blushes, eye shadows, mascaras, nail varnishes, nail lacquers, and non permanent dyeing compositions for the hair.

Composition Example 1

Sunscreen Composition 1

| Phase A | |
|---|---|
| Deionized water | 60.0% |
| Disodium EDTA | 0.10% |
| Glycerin | 1.5% |
| NaCl | 3.0% |
| Butylene glycol | 2.5% |
| Phase B | |
| Active ingredient | 8.75% |
| Octyl salicylate | 5% |
| Aluminum stearate | 5% |
| Cyclomethicone + Dimethicone | 10% |
| Cetyl dimethicone | 1% |
| Cyclomethicone | 2% |
| ABIC-EM 97 | 1% |
| Fragrance | 0.15% |
| TOTAL | 100.00% |

Procedure

Phase B ingredients were combined. The mixture was stirred and heated to 70-75° C. Phase A ingredients were combined. The mixture was heated to 70-75° C. while stirring. Phase B was added to phase A while stirring. Preservative was added. The mixture was stirred, allowing to cool to room temperature.

Composition Example 2

Sunscreen Oil/Water Spray Lotion

| | % w/w |
|---|---|
| Phase A-1 | |
| Active ingredient 1 | 7.50% |
| Active ingredient 2 | 2.50% |
| Dicapryl ether | 4.50% |
| Dimethicone | 2.00% |
| Stearyl alcohol | 0.60% |
| PPG-2 Ceteareth-9[1] | 0.40% |
| Steareth-10 | 0.50% |
| Glyceryl stearate + PEG-100 stearate[2] | 2.80% |
| Phase A-2 | |
| Titanium dioxide + Simethicone + Alumina[3] | 5.00% |
| Phase B-1 | |
| Demineralized water | 66.10% |
| Chitosan + water[4] | 2.00% |
| Glycerin USP | 2.50% |
| Dimethicone copolyol phosphate | 2.50% |
| Phase B-2 | |
| Polyquaternium 37 + Mineral oil + PPG-1 trideceth-6[5] | 0.40% |
| Phase C | |
| Propylene glycol + DMDM Hydantoin + Methylparaben + Propylparaben[6] | 0.70% |
| TOTAL | 100.00% |

[1] Eumulgin ® L (Henkel)
[2] Ariacel ® 165 (ICI)
[3] Eusolex ® T-2000 (Rona)
[4] Hydagen ® CMF (Henkel)
[5] Salcare ® SC 95 (Ciba)
[6] Paragon ® II (McIntyre)

Procedure

The A-1 ingredients were combined; the mixture was stirred and heated to 60° C. until all solids were dissolved. A-2 was dispersed in A-1 with agitation. The B-1 ingredients were combined; the mixture was stirred and heated to 60° C. B-2 was dispersed in B-1 with agitation. A was added to B while stirring vigorously. The mixture was gently homogenized allowing to cool to 40° C. C was added to A/B; the mixture was gently homogenized until mixture was uniform. The mixture was stirred with another mixer allowing mixture to reach 25° C. prior to packaging. Dispensing is made conveniently by a high shear pump spray device.

Composition Example 3

Sunscreen Cream

| | % w/w |
|---|---|
| Phase A | |
| Deionized water | 39.73% |
| Carbomer (2% aq. solution) | 15.00% |
| Propylene glycol | 5.00% |
| Methylparaben | 0.20% |

|  | % w/w |
|---|---|
| Propylparaben | 0.10% |
| Triethanolamine (99%) | 0.45% |
| Tetrasodium EDTA | 0.02% |
| Phase B | |
| Active ingredient 1 | 5.00% |
| Active ingredient 2 | 3.00% |
| Active ingredient 3 | 4.50% |
| Glyceryl stearate + PEG-100 stearate[1] | 1.00% |
| Cyclomethicone | 5.00% |
| Glyceryl stearate | 4.00% |
| Stearic acid | 2.50% |
| Isostearyl isostearate | 10.00% |
| Hydrogenated castor oil | 2.00% |
| C12-15 alcohol benzoates[2] | 2.50% |
| TOTAL | 100.00% |

[1]Ariacel ® 165 (ICI)
[2]Finsolv ® TN (Finetex)

Procedure

Phase A ingredients were added to a main vessel under impeller agitation. The mixture was heated to 75-80° C. Phase B ingredients were combined; the suspension was heated and mixed to 85° C. Phase B was added slowly to batch and mixed for 15 minutes at 85° C. After removing the mixture from heat, it was switched to paddle mixing and cooled to room temperature.

Composition Example 4

Water/Oil Broad Spectrum Sunscreen Lotion

|  | % w/w |
|---|---|
| Active ingredient 1 | 7.50% |
| Active ingredient 2 | 5.00% |
| Octyl stearate | 2.00% |
| Dicapryl ether | 3.00% |
| Cyclomethicone | 4.00% |
| Dimethicone | 2.00% |
| PEG-30 Dipolyhydroxystearate[1] | 1.30% |
| Laurylmethicone copolyol | 2.30% |
| Behanemidopropyl dimethylamine behenate | 0.50% |
| Titanium dioxide + Alumina + Simethicone[2] | 8.00% |
| Deionized water qs | 61.00% |
| Propylene glycol | 2.00% |
| NaCl | 0.80% |
| Propylene glycol + DMDM Hydantoin + Methylparaben + Propylparaben[3] | 0.60% |
| TOTAL | 100.00% |

[1]Ariacel ® P135 (ICI)
[2]Eusolex ® T-2000 (Rona)
[3]Paragon ® II (McIntyre)

Composition Example 5

UVA/UVB Sun Protection Cream with Avobenzone

|  | % w/w |
|---|---|
| Phase A-1 | |
| Water (demineralized) | 67.80% |
| Disodium EDTA | 0.05% |
| Propylene glycol | 3.00% |
| Methylparaben | 0.15% |
| Phase A-2 | |
| Carbomer | 0.20% |
| Phase B | |
| Isopropyl myristate | 2.00% |
| Cetyl alcohol + Glyceryl stearate + PEG-75 Stearate + Cetech 20 + Stereth 201[1] | 4.00% |
| Active ingredient | 3.50% |
| Homomethyl salicylate | 7.00% |
| Octyl salicylate | 7.00% |
| Avobenzone | 3.00% |
| Dimethicone | 1.00% |
| C30-38 Olefin + Isopropyl maleate + MA copolymer[2] | 1.00% |
| Phase C | |
| Triethanolamine (99%) | 0.30% |
| Phase D | |
| Preservatives | qs |
| TOTAL | 100.00% |

[1]Emulium Delta ® (Gattefosse)
[2]Performa ® V 1608 (New Phase Technologies)

Procedure

Phase A-1 ingredients were combined; the mixture was heated to 50° C. while stirring until methylparaben was dissolved. A-2 was dispensed in A-1 with a sifter. The resulting mixture A was heated to 65° C. Phase B ingredients were combined; the mixture was heated to 65-70° C. while stirring until solids were dissolved. B was added to A. The mixture was homogenized and C was added at 55-60° C. Homogenizing was continued allowing mixture to cool to 40-45° C. Phase D was added; the mixture was stirred with propeller mixer until uniform. pH was adjusted to 6.5-7.0 with triethanolamine.

Composition Example 6

Oil/Water Sunscreen Lotion

|  | % w/w |
|---|---|
| Phase A | |
| Active ingredient | 3.00% |
| Isopropyl myristate | 4.00% |
| C12-15 Alkyl benzoate[1] | 4.00% |
| Cetyl alcohol | 1.50% |
| Steareth-2 | 2.00% |
| Steareth-21 | 2.50% |
| Dimethicone | 0.50% |
| Phase B | |
| Deionized water | 81.07% |
| Acrylates/C10-30 Alkyl Acrylates crosspolymer[2] | 0.20% |
| Phase C | |
| Triethanolamine (99%) | 0.23% |
| Phase D | |
| Phenoxyethanol + Isopropylparaben + Isobutylparaben + Butylparaben[3] | 1.00% |
| TOTAL | 100.00% |

[1]Finsolv ® TN (Finetex)
[2]Carbopol ® ETD 2020 (B F Goodrich)
[3]Liquapar ® PR (Sutton)

Procedure

Phase B was prepared by dispersing Carbopol in water. The dispersion was heated to 70-75° C. Phase A ingredients were combined. The mixture was stirred and heated to 70-75° C. Phase B was added to phase A while stirring. Phase C was added. The mixture was homogenized until it cooled to 45-40° C. Phase D was added. The mixture was stirred allowing to cool to room temperature.

Composition Example 7

Oil/Water Sunscreen Lotion with Avobenzone

|  | % w/w |
|---|---|
| Phase A | |
| Active ingredient | 3.00% |
| Avobenzone | 3.00% |
| Isopropyl myristate | 4.00% |
| C12-15 Alkyl benzoate[1] | 4.00% |
| Cetyl alcohol | 1.50% |
| Steareth-2 | 2.00% |
| Steareth-21 | 2.50% |
| Dimethicone | 0.50% |
| Phase B | |
| Deionized water | 78.07% |
| Acrylates/C10-30 Alkyl Acrylates crosspolymer[2] | 0.20% |
| Phase C | |
| Triethanolamine (99%) | 0.23% |
| Phase D | |
| Phenoxyethanol + Isopropylparaben + Isobutylparaben + Butylparaben[3] | 1.00% |
| TOTAL | 100.00% |

[1]Finsolv ® TN (Finetex)
[2]Carbopol ® ETD 2020 (B F Goodrich)
[3]Liquapar ® PR (Sutton)

Procedure

Phase B was prepared by dispersing Carbopol in water. The dispersion was heated to 70-75° C. Phase A ingredients were combined. The mixture was stirred and heated to 70-75° C. Phase B was added to phase A while stirring. Phase C was added. The mixture was homogenized until it cooled to 45-40° C. Phase D was added. The mixture was stirred allowing to cool to room temperature.

Composition Example 8

Sun Care Lipstick

|  | % w/w |
|---|---|
| Active ingredient | 7.00% |
| Microcrystalline wax | 5.00% |
| Glyceryl trihydroxystearate | 5.00% |
| Ozokerite | 3.40% |
| Polyglycerolated beeswax | 2.10% |
| Acetylated lanolin | 19.45% |
| Lanolin oil | 19.10% |
| Avocado oil | 18.99% |
| Butene/isobutene copolymer | 14.34% |
| Castor oil | 4.81% |
| Ascorbyl palmitate | 0.50% |
| Mixture of tocopherols in soybean oil (50/50) | 0.31% |
| TOTAL | 100.00% |

Composition Example 9

Sunscreen Gel

|  | % w/w |
|---|---|
| Active ingredient 1 | 8.00% |
| Active ingredient 2 | 6.00% |
| TiO2 | 7.00% |
| Glycerol | 5.00% |
| PEG-25 p-aminobenzoic acid | 5.00% |
| Acrylates/C10-30 Alkyl Acrylates crosspolymer[1] | 0.40% |
| Imidazolidinylurea | 0.30% |
| Hydroxyethylcellulose | 0.25% |
| Sodium methylparaben | 0.25% |
| Disodium EDTA | 0.20% |
| Fragrance | 0.15% |
| Sodium propylparaben | 0.15% |
| Sodium hydroxide | 0.10% |
| Water | qs |
| TOTAL | 100.00% |

[1]Carbopol ® ETD 2020 (B F Goodrich)

Composition Example 10

Sunscreen Cream

|  | % w/w |
|---|---|
| Active ingredient 1 | 7.00% |
| Active ingredient 2 | 7.00% |
| TiO2 | 8.00% |
| ZnO2 | 5.00% |
| PEG-7 hydrogenated castor oil | 6.00% |
| Mineral oil | 6.00% |
| Isopropyl palmitate | 5.00% |
| Imidazolidinylurea | 0.30% |
| Jojoba oil | 3.00% |
| PEG-45 dodecyl glycol copolymer | 2.00% |
| Magnesium stearate | 0.60% |
| Tocopheryl acetate | 0.50% |
| Methylparaben | 0.25% |
| Disodium EDTA | 0.20% |
| Propylparaben | 0.15% |
| Water | qs |
| TOTAL | 100.00% |

Composition Example 11

Water-Resistant Sunscreen Cream

|  | % w/w |
|---|---|
| Active ingredient 1 | 8.00% |
| Active ingredient 2 | 7.00% |
| TiO2 | 3.00% |
| PEG-7 hydrogenated castor oil | 5.00% |
| Propylene glycol | 5.00% |

-continued

|  | % w/w |
| --- | --- |
| Isopropyl palmitate | 4.00% |
| Caprylic/Capric triglyceride | 4.00% |
| Glycerol | 4.00% |
| Jojoba oil | 3.00% |
| PEG-45 dodecyl glycol copolymer | 1.50% |
| Dimethicone | 1.50% |
| Magnesium sulfate | 0.70% |
| Magnesium stearate | 0.50% |
| Fragrance | 0.15% |
| Water | qs |
| TOTAL | 100.00% |

Composition Example 12

Sunscreen Milk

|  | % w/w |
| --- | --- |
| Active ingredient 1 | 4.50% |
| Active ingredient 2 | 4.00% |
| Mineral oil | 10.00% |
| PEG-7 hydrogenated castor oil | 6.00% |
| Isopropyl palmitate | 5.00% |
| Caprylic/Capric triglyceride | 3.00% |
| Jojoba oil | 3.00% |
| PEG-45 dodecyl glycol copolymer | 2.00% |
| Magnesium sulfate | 0.70% |
| Magnesium stearate | 0.60% |
| Tocopheryl acetate | 0.50% |
| Glycerol | 3.00% |
| Methylparaben | 0.25% |
| Propylparaben | 0.15% |
| Tocopherol | 0.05% |
| Water | qs |
| TOTAL | 100.00% |

Composition Example 13

Sunscreen Makeup Powder

|  | % w/w |
| --- | --- |
| Active ingredient 1 | 0.12% |
| Active ingredient 2 | 0.08% |
| Talc | 76.00% |
| Polyethylene powder | 4.00% |
| Magnesium carbonate | 8.76% |
| Isopropyl myristate | 1.20% |
| Liquid petrolatum | 1.20% |
| Sorbitol | 4.00% |
| Bordeaux 5B pigment | 0.52% |
| Victoria Blue Lake pigment | 0.12% |
| Titanium mica | 4.00% |
| TOTAL | 100.00% |

Composition Example 14

Sunscreen Nail Varnish

|  | % w/w |
| --- | --- |
| Active ingredient | 0.30% |
| Nitrocellulose | 6.43% |
| Toluensulfonamide formaldehyde resin | 5.81% |
| Acetyltributyl citrate | 3.83% |
| Butyl acetate | 12.85% |
| Ethyl acetate | 5.54% |
| Stearalkonium hectorite | 0.80% |
| Citric acid | 0.04% |
| Victoria Blue Lake pigment | 0.01% |
| TiO2 | 0.45% |
| Bordeaux 5B pigment | 0.04% |
| Titanium mica | 0.35% |
| Isopropyl alcohol | 4.60% |
| Toluene | qs |
| TOTAL | 100.00% |

The invention claimed is:

1. An organosilicon progressive photoprotective polymer obtainable by a process which comprises the reaction of a monomer of formula (I):

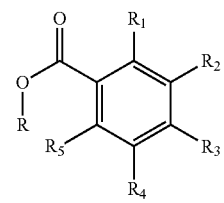

(I)

wherein:
R is selected from the group consisting of (i), (ii), (iii), and (iv):

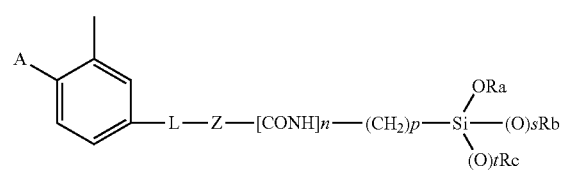

(i)

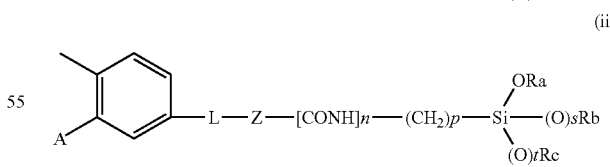

(ii)

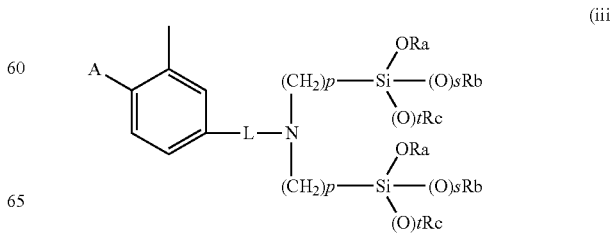

(iii)

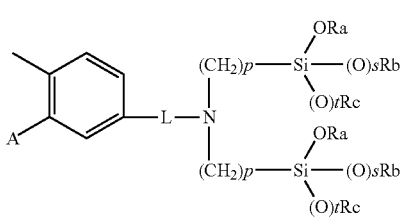

(iv)

$R_1$, $R_2$, $R_3$, $R_4$ and $R_5$ are independently selected from the group consisting of H, linear or branched $(C_1\text{-}C_6)$alkyl, $(C_3\text{-}C_6)$cycloalkyl, $OR_6$, $NH_2$, $NHR_7$, $NR_8R_9$, COOH, $COOR_{10}$, $CONH_2$, $CONHR_{11}$, $CONR_{12}R_{13}$, $SO_2NH_2$, $SO_2NHR_{14}$, and $SO_2NR_{15}R_{16}$;

$R_6$ is linear or branched $(C_1\text{-}C_6)$alkyl or $(C_3\text{-}C_6)$cycloalkyl;
$R_7$ is linear or branched $(C_1\text{-}C_6)$alkyl or $(C_3\text{-}C_6)$cycloalkyl;
$R_8$ is linear or branched $(C_1\text{-}C_6)$alkyl or $(C_3\text{-}C_6)$cycloalkyl;
$R_9$ is linear or branched $(C_1\text{-}C_6)$alkyl or $(C_3\text{-}C_6)$cycloalkyl; or $R_8$ and $R_9$ taken together with the nitrogen atom to which they are attached form a pyrrolidine, piperidine or morpholine ring;
$R_{10}$ is linear or branched $(C_1\text{-}C_6)$alkyl or $(C_3\text{-}C_6)$cycloalkyl;
$R_{11}$ is linear or branched $(C_1\text{-}C_6)$alkyl or $(C_3\text{-}C_6)$cycloalkyl;
$R_{12}$ is linear or branched $(C_1\text{-}C_6)$alkyl or $(C_3\text{-}C_6)$cycloalkyl;
$R_{13}$ is linear or branched $(C_1\text{-}C_6)$alkyl or $(C_3\text{-}C_6)$cycloalkyl; or $R_{12}$ and $R_{13}$ taken together with the nitrogen atom to which they are attached form a pyrrolidine, piperidine or morpholine ring;
$R_{14}$ is linear or branched $(C_1\text{-}C_6)$alkyl or $(C_3\text{-}C_6)$cycloalkyl;
$R_{15}$ is linear or branched $(C_1\text{-}C_6)$alkyl or $(C_3\text{-}C_6)$cycloalkyl;
$R_{16}$ is linear or branched $(C_1\text{-}C_6)$alkyl or $(C_3\text{-}C_6)$cycloalkyl; or $R_{15}$ and $R_{16}$ taken together with the nitrogen atom to which they are attached form a pyrrolidine, piperidine or morpholine ring;
A is H, linear or branched $(C_1\text{-}C_6)$alkyl, $(C_3\text{-}C_6)$cycloalkyl, $OR'_1$, $NH_2$, $NHR'_2$ or $NR'_3R'_4$;
L is a single bond, —$CH_2$—, or —$CH_2$—$CH(R_L)$—
Z is NH or O;
Ra is linear or branched $(C_1\text{-}C_6)$alkyl, linear or branched $(C_2\text{-}C_6)$alkenyl, $(C_3\text{-}C_6)$cycloalkyl or phenyl;
Rb is linear or branched $(C_1\text{-}C_6)$alkyl, linear or branched $(C_2\text{-}C_6)$alkenyl, $(C_3\text{-}C_6)$cycloalkyl or phenyl;
Rc is linear or branched $(C_1\text{-}C_6)$alkyl, linear or branched $(C_2\text{-}C_6)$alkenyl, $(C_3\text{-}C_6)$cycloalkyl or phenyl;
$R'_1$ is linear or branched $(C_1\text{-}C_6)$alkyl or $(C_3\text{-}C_6)$cycloalkyl;
$R'_2$ is linear or branched $(C_1\text{-}C_6)$alkyl or $(C_3\text{-}C_6)$cycloalkyl;
$R'_3$ is linear or branched $(C_1\text{-}C_6)$alkyl or $(C_3\text{-}C_6)$cycloalkyl;
$R'_4$ is linear or branched $(C_1\text{-}C_6)$alkyl or $(C_3\text{-}C_6)$cycloalkyl; or $R'_3$ and $R'_4$ taken together with the nitrogen atom to which they are attached form a pyrrolidine, piperidine or morpholine ring;
$R_L$ is H, linear or branched $(C_1\text{-}C_6)$alkyl or $(C_3\text{-}C_6)$cycloalkyl;
n is an integer selected from 0 and 1;
p is an integer selected from 2, 3 and 4;
s is an integer selected from 0 and 1;
t is an integer selected from 0 and 1;
with a compound of formula (IV):

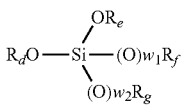

(IV)

wherein:
Rd is a linear or branched $(C_1\text{-}C_6)$alkyl;
Re, Rf and Rg are independently a linear or branched $(C_1\text{-}C_6)$alkyl, linear or branched $(C_2\text{-}C_6)$alkenyl, $(C_3\text{-}C_6)$cycloalkyl or phenyl,
$w_1$ and $w_2$ are independently 0 or 1,
in an alkanol/water mixture, wherein the alkanol is a linear or branched alkanol having 1 to 6 carbon atoms,
and in the presence of a nitrogen-containing basic compound selected from the group consisting of ammonia, mono-alkylamine, di-alkylamine, tri-alkylamine, mono-alkanolamine, di-alkanolamine, and tri-alkanolamine, wherein both alkyl and alkanol groups are linear or branched having 1 to 6 carbon atoms,
characterized in that the organosilicon progressive photoprotective polymer exhibits a micro- or nanoparticle form.

2. A cosmetic or dermatological composition comprising an organosilicon progressive photoprotective polymer as defined in claim 1 or a mixture thereof.

3. The cosmetic or dermatological composition according to claim 2, comprising an effective amount of an organosilicon polymer or a mixture thereof susceptible to be photochemically converted in situ to sunscreen compounds with enhanced protection ability.

4. The cosmetic or dermatological composition according to claim 2, characterized in that the content of polymers ranges from 0.01% to 40% by weight, based on the total weight of the composition.

5. The cosmetic or dermatological composition according to claim 2, further comprising a sunscreen compound selected from avobenzone, 2-ethylhexyl-p-methoxycinnamate, oxybenzone, octyldimethyl p-aminobenzoic acid, dioxybenzone, ethyl-4-[bis(hydroxypropyl)]aminobenzoate, 2-ethylhexyl-2-cyan-3,3-diphenylacrylate, 2-ethylhexylsalicylate, glyceryl p-aminobenzoate, 3,3,5-trimethylcyclohexylsalicylate, methylanthranylate, p-dimethylaminobenzoic acid, 2-ethylhexyl p-dimethylaminobenzoate, 2-phenylbenzimidazole-5-sulfonic acid, 2-p-dimethylaminophenyl-5-sulfoniumbenzoxazoic acid, sulisobenzone, hexyl 2-(4-diethylamino-2-hydroxybenzoyl)benzoate, 2-(4-methylbenzyliden)-camphor, and 4-isopropyldibenzoylmethane.

6. The organosilicon progressive photoprotective polymer according to claim 1, wherein the process by which said polymer can be obtained is further characterized by the presence of a nitrogen-containing basic compound selected from the group consisting of ammonia, mono-alkylamine, di-alkylamine, tri-alkylamine, mono-alkanolamine, di-alkanolamine, and tri-alkanolamine, wherein both alkyl and alkanol groups are linear or branched having 1 to 6 carbon atoms.

7. The organosilicon progressive photoprotective polymer according to claim 1, wherein the process by which said polymer can be obtained is further characterized in that the alkanol/water mixture is an ethanol/water mixture.

* * * * *